United States Patent [19]
Souchelnytokyi et al.

[11] Patent Number: 6,103,869
[45] Date of Patent: Aug. 15, 2000

[54] SMAD2 PHOSPHORYLATION AND INTERACTION WITH SMAD4

[75] Inventors: Serhiy Souchelnytokyi; Kiyoshi Tamaki; Ulla Engeström; Christer Wernstedt; Ester Piek; Peter ton Dijke; Carl-Henrik Heldin, all of Uppsala, Sweden

[73] Assignee: Ludwig Institute for Cancer Research, New York, N.Y.

[21] Appl. No.: 09/082,039

[22] Filed: May 20, 1998

Related U.S. Application Data

[60] Provisional application No. 60/047,807, May 20, 1997, and provisional application No. 60/081,313, Apr. 10, 1998.

[51] Int. Cl.$^7$ .................................................. C07K 14/00
[52] U.S. Cl. ......................... 530/330; 530/329; 530/328; 530/327; 530/326; 530/300; 530/350
[58] Field of Search ................................. 530/350, 300, 530/326, 328, 329, 330, 327

[56] References Cited

PUBLICATIONS

Roberts et al., *Growth Factors*, 8:1–9, 1993.
Lin and Lodish, *Trends Cell Biol.*, 11:972–978., 1993.
Derynck, *Trends Biochem. Sci.*, 19:548–553, 1994.
Massague and Weis–Garcia, *Cancer Surv.* 27:41–64, 1996.
ten Dijke et al., *Curr. Opin. Cell Biol.*, 8:139–145, 1996.
Wrana et al., *Nature*, 370:341–347, 1994.
Wieser et al., *EMBO J.*, 14:2199–2208, 1995.
Sekelsky et al., *Genetics*, 139:1347–1358, 1995.
Savage et al., *Proc. Natl. Acad. Sci. USA*, 93:790–794, 1996.
Wiersdorf et al., *Development*, 122:2153–2163, 1996.
Newfeld et al., *Development*, 122:2099–2108, 1996.
Hoodless et al., *Cell*, 85:489–500, 1996.
Derynck et al., *Cell*, 87:173, 1996.
Wrana and Attisano, *Trends Genet.*, 12:493–496, 1996.
Hahn et al., *Science*, 271:350–353, 1996.
Riggins et al., *Nature Genet.*, 13:347–349, 1996.
Eppert et al., *Cell*, 86:543–552, 1996.
Massague, *Cell* 85:947–950, 1996.
Derynck and Zhang, *Curr. Biol.*, 6:1226–1229, 1996.
Liu et al., *Nature*, 381:620–623, 1996.
Meersseman et al., *Mech. Dev.*, 61:127–140, 1997.
Graff et al., *Cell*, 85:479–487, 1996.
Baker and Harland, *Genes & Dev.*, 10:1880–1889 1996.
Thomsen, *Development*, 122:2359–2366, 1996.
Lechleider et al., *J. Biol. Chem.*, 271:17617–17620, 1996.
Yingling et al., *Proc. Natl. Acad. Sci. USA*, 93:8940–8944, 1996.
Zhang et al., *Nature*, 383:168–172, 1996.
Macias–Silva et al., *Cell*, 87:1215–1224, 1996.
Nakao et al., *J. Biol. Chem.*, 272:2896–2900, 1996.
Lagna et al., *Nature*, 383:832–836, 1996.
Zhang et al., *Curr. Biol.*, 7:270–276, 1997.
de Winter et al., *Oncogene*, 14:1891–1900, 1997.
Chen et al., *Nature*, 383:691–696, 1996.
ten Dijke et al., *Science*, 264:101–104, 1994.
Souchelnytskyi et al., *EMBO J.*, 15:6231–6240, 1996.
Liu et al., *Proc. Natl. Acad. Sci. USA* 94:10669–10674, 1997.
Abdollah et al., *J. Biol. Chem.*, 272:27678–27685, 1996.
Kretschmar et al., *Genes & Dev.*, 11:984–995, 1997.

*Primary Examiner*—Karen Cochrane Carlson
*Attorney, Agent, or Firm*—Wolf, Greenfield & Sacks, P.C.

[57] ABSTRACT

The invention describes amino acid residues of the Smad2 protein which are important for phosphorylation and activity, and Smad2 polypeptide fragments and biologically functional variants thereof. Included and dominant-negative variants of Smad2 and antibodies relating thereto. Also included are nucleic acids which encode such variants. Antibodies which selectively bind pathway-restricted Smad proteins phosphorylated at the C-terminal tail also are provided. Methods and products for using such nucleic acids and polypeptides also are provided.

16 Claims, 10 Drawing Sheets

| TGF-β | − | + | | | |
|---|---|---|---|---|---|
| TβR-II/TβR-I | + | | | | |
| Smad2 | + | | | | |
| Smad7 | + | 0.1 μg | 1 μg | − | 0.1 μg | 1 μg |

← Smad2

SMAD2 PHOSPHORYLATION AND INTERACTION WITH SMAD4

RELATED APPLICATIONS

This application claims priority under 35 U.S.C. §119 from U.S. provisional application Ser. No. 60/047,807, filed May 20, 1997, and from U.S. provisional application Ser. No. 60/081,313, filed Apr. 10, 1998.

FIELD OF THE INVENTION

This invention relates to nucleic acids and encoded polypeptides which interact with the TGF-β receptor complex and which is a negative regulator of TGF-β signaling. The invention also relates to agents which bind the nucleic acids or polypeptides. The invention further relates to methods of using such nucleic acids and polypeptides in the treatment and/or diagnosis of disease.

BACKGROUND OF THE INVENTION

During mammalian embryogenesis and adult tissue homeostasis transforming growth factor β (TGF-β) performs pivotal tasks in intercellular communication (Roberts et al., *Growth Factors*, 8:1–9, 1993). The cellular effects of theis pleiotropic factor are exerted by ligand-induced hetero-oligomerization of two distantly related type I and type II serine/threonine kinase receptors, TβR-I and TβR-II, respectively (Lin and Lodish, *Trends Cell Biol.*, 11: 972–978., 1993; Derynck, *Trends Biochem. Sci.*, 19:548–553, 1994; Massague and Weis-Garcia, *Cancer Surv.* 27:41–64, 1996; ten Dijke et al., *Curr. Opin. Cell Biol.*, 8:139–145, 1996). The two receptors, which both are required for signaling, act in sequence; TβR-I is a substrate for the constitutively active TβR-II kinase (Wrana et al., *Nature*, 370:341–347, 1994; Wieser et al., *EMBO J.*, 14:2199–2208, 1995). TGF-β forms part of a large family of structurally related proteins which include activins and bone morphogenetic proteins (BMPs) that signal in a similar fashion, each employing distinct complexes of type I and type II serine/threonine kinase receptors (Lin and Lodish, 1993; Derynck, 1994; Massague and Weis-Garcia, 1996; ten Dijke et al., 1996).

Genetic studies of TGF-β-like signaling pathways in Drosophila and Caenorhabditis elegans have led to the identification of mothers against dpp (Mad) (Sekelsky et al., *Genetics*, 139:1347–1358, 1995) and sma (Savage et al., *Proc. Nat. Acad. Sci. USA*, 93:790–794, 1996) genes, respectively. The products of these related genes perform essential functions downstream of TGF-β-like ligands acting via serine/threonine kinase receptors in these organisms (Wiersdorf et al., *Development*, 122:2153–2163,1996; Newfeld et al., *Development*, 122:2099–2108, 1996; Hoodless et al., *Cell*, 85:489–500, 1996). Vertebrate homologs of Mad and sma have been termed Smads (Derynck et al., *Cell*, 87:173, 1996) or MADR genes (Wrana and Attisano, *Trends Genet.*, 12:493–496, 1996). Genetic alterations in Smad2 and Smad4/DPC4 have been found in specific tumor subsets, and thus Smads may function as tumor suppressor genes (Hahn et al., *Science*, 271:350–353, 1996; Riggins et al., *Nature Genet.*, 13:347–349, 1996; Eppert et al., *Cell*, 86:543–552, 1996). Smad proteins share two regions of high similarity, termed MH1 and MH2 domains, connected with a variable proline-rich sequence (Massague, *Cell* 85:947–950, 1996; Derynck and Zhang, *Curr. Biol.*, 6:1226–1229, 1996). The C-terminal part of Smad2, when fused to a heterologous DNA-binding domain, was found to have transcriptional activity (Liu et al., *Nature*, 381:620–623, 1996; Meersseman et al., *Mech. Dev.*, 61:127–140, 1997). The intact Smad2 protein when fused to a DNA-binding domain, was latent, but transcriptional activity was unmasked after stimulation with ligand (Liu et al., 1996).

Different Smads specify different responses using functional assays in Xenopus. Whereas Smad1 induces ventral mesoderm, a BMP-like response, Smad2 induces dorsal mesoderm, an activin/TGF-β-like response (Graff et al., *Cell*, 85:479–487, 1996; Baker and Harland *Genes & Dev.*, 10:1880–1889 1996; Thomsen, *Development*, 122:2359–2366, 1996). Upon ligand stimulation Smads become phosphorylated on serine and threonine residues; BMP stimulates Smad1 phosphorylation, whereas TGF-β induces Smad2 and Smad3 phosphorylation (Hoodless et al., 1996; Liu et al., 1996; Eppert et al., 1996; Lechleider et al., *J. Biol. Chem.*, 271:17617–17620, 1996; Yingling et al., *Proc. Natl. Acad. Sci. USA*, 93:8940–8944, 1996; Zhang et al., *Nature*, 383:168–172, 1996; Macías-Silva et al., *Cell*, 87:1215–1224, 1996; Nakao et al., *J. Biol. Chem.*, 272:2896–2900, 1996).

Smad4 is a common component of TGF-β, activin and BMP signaling (Lagna et al., *Nature*, 383:832–836, 1996; Zhang et al., *Curr. Biol.*, 7:270–276, 1997; de Winter et al., *Oncogene*, 14:1891–1900, 1997). Smad4 phosphorylation has thus far been reported only after activin stimulation of transfected cells (Lagna et al., 1996). After stimulation with TGF-β or activin Smad4 interacts with Smad2 or Smad3, and upon BMP challenge a heteromeric complex of Smad4 and Smad1 has been observed (Lagna et al., 1996). Upon ligand stimulation, Smad complexes translocate from the cytoplasm to the nucleus (Hoodless et al., 1996; Liu et al., 1996; Baker and Harland, 1996; Macías-Silva et al., 1996), where they, in combination with DNA-binding proteins, may regulate gene transcription (Chen et al., *Nature*, 383:691–696, 1996).

SUMMARY OF THE INVENTION

The invention provides isolated Smad2 polypeptides and agents which bind such polypeptides, including antibodies. The invention also provides isolated nucleic acid molecules which encode the foregoing polypeptides, unique fragments of those molecules, expression vectors containing the foregoing, and host cells transfected with those molecules. The foregoing can be used in the diagnosis or treatment of conditions characterized by TGF-β signal transduction. The invention also provides methods for identifying pharmacological agents useful in the diagnosis or treatment of such conditions. Here, the identification of Smad2 amino acid residues phosphorylated in vivo is reported.

According to one aspect of the invention, an isolated Smad2 polypeptide is provided. The polypeptide has the amino acid sequence of SEQ ID NO:2 or its human homolog except that the polypeptide includes a mutation comprising a non-serine amino acid located at one or more of amino acids 464, 465 and 467. In certain embodiments, the isolated Smad2 polypeptide compises a mutation which is located at a position or positions selected from the group consisting of 464; 465; 467; 464 and 465; 464 and 467; 465 and 467; and 464, 465 and 467. Preferably the isolated Smad2 polypeptide comprises a mutation or mutations of the serine residues to alanine residues (e.g., Ser465A) or aspartic acid residues (e.g., Ser465D) such as those selected from the group consisting of Ser464A; Ser465A; Ser467A; Ser464A and Ser465A; Ser464A and Ser467A; Ser465A and Ser467A; Ser464A, Ser465A and Ser467A; Ser465D; Ser467D; and Ser465D and Ser467D.

In other embodiments, the foregoing isolated polypeptide consists of a fragment or variant of the foregoing which retains the activity of the foregoing.

According to still another aspect of the invention, nucleic acid molecules which encode the foregoing polypeptides are provided. The nucleic acids can be composed of natural and/or non-natural nucleotides and linked with natural and/or non-natural internucleoside bonds.

According to still another aspect of the invention, the invention involves expression vectors, and host cells transformed or transfected with such expression vectors, comprising the nucleic acid molecules described above.

According to another aspect of the invention, there are provided isolated Smad4 binding polypeptides comprising the amino acid sequence of SEQ ID NO:3, which selectively bind a Smad4 protein or fragment thereof, provided that the isolated polypeptide is not wild type Smad2. In certain embodiments, the isolated Smad4 binding polypeptide comprises the C-terminal 4, 5, 6, 7, 8, 9, 10, 11, 12, 13, 14, 15, 16, 17, 18, 19, or 20 amino acids of SEQ ID NO:2. Preferably, the isolated Smad4 binding polypeptide of comprises the amino acid sequence of SEQ ID NO:4. In other preferred embodiments, the foregoing isolated Smad4 binding polypeptides are phosphorylated on one or more amino acids selected from the group consisting of Ser464, Ser465, Ser467, Ser464/Ser465, Ser464/Ser467, Ser465/Ser467 and Ser464/Ser465/Ser467.

According to yet another aspect of the invention, the invention involves an isolated polypeptide which binds selectively any of the foregoing isolated polypeptides, provided that the isolated polypeptide is not TβR-I, TβR-II or Smad4. In preferred embodiments, the isolated binding polypeptides include antibodies and fragments of antibodies (e.g., Fab, F(ab)$_2$, Fd and antibody fragments which include a CDR3 region which binds selectively to the polypeptides of the invention). Particularly preferred antibodies include monoclonal antibodies.

In another aspect of the invention, an isolated polypeptide is provided which binds selectively to at least one pathway-restricted Smad polypeptide or fragment thereof having the C-terminal amino acid sequence of SEQ ID NO:5. The pathway-restricted Smad polypeptide or fragment thereof is phosphorylated on at least one serine residue of SEQ ID NO:5, and the isolated polypeptide is not TβR-I, TβR-II or Smad4. In certain embodiments, the pathway restricted Smad polypeptide is selected from the group consisting of Smad1, Smad3, Smad5 and Smad9. In other embodiments, the at least one serine residue is selected from the group consisting of the second serine residue, the third serine residue and the second and third serine residues. In preferred embodiments, the isolated binding polypeptides include antibodies and fragments of antibodies (e.g., Fab, F(ab)$_2$, Fd and antibody fragments which include a CDR3 region which binds selectively to pathway-restricted Smad polypeptides). Particularly preferred antibodies include monoclonal antibodies. In certain embodiments, the antibody or antibody fragment binds selectively to one of the pathway restricted Smad polypeptides.

According to still another aspect of the invention, methods for inhibiting TGF-β signal transduction in a mammalian cell are provided. The methods involve contacting a mammalian cell with an amount of an inhibitor of phosphorylation of endogenous Smad2 effective to reduce TGF-β signal transduction in the mammalian cell. In certain embodiments of the foregoing methods, the inhibitor is a dominant negative Smad2 polypeptide, such as the foregoing Smad2 polypeptides which include a mutation at one or more of residues 464, 465 and 467.

The invention in still another aspect provides compositions comprising a Smad2 polypeptide which includes a mutation at one or more of residues 464, 465 and 467, and a pharmaceutically acceptable carrier.

The invention in a further aspect involves a method for decreasing TGF-β signal transduction activity in a subject. An agent that selectively binds to a TGF-β receptor and blocks TGF-β signaling is administered to a subject in need of such treatment, in an amount effective to decrease Smad2 TGF-β signal transduction activity in the subject. Preferred agents are Smad2 polypeptides which include a mutation at one or more of serines 464, 465 and 467, particularly those which are substituted with alanines or aspartic acids.

According to another aspect of the invention, methods are provided for identifying lead compounds for a pharmacological agent useful in the diagnosis or treatment of disease associated with Smad2/TGF-β receptor interaction. The methods involve forming a mixture of a Smad2 polypeptide comprising a mutation at one or more of serines 464, 465 and 467, a TGF-β receptor, and a candidate pharmacological agent. The mixture is incubated under conditions which, in the absence of the candidate pharmacological agent, permit a first amount of specific binding of the TGF-β receptor by the Smad2 polypeptide. A test amount of the specific binding of the TGF-β receptor by the Smad2 polypeptide then is detected. Detection of a reduction in the foregoing activity in the presence of the candidate pharmacological agent indicates that the candidate pharmacological agent is a lead compound for a pharmacological agent which disrupts the Smad2/TGF-β receptor interaction. Detection of an increase in the foregoing activities in the presence of the candidate pharmacological agent indicates that the candidate pharmacological agent is a lead compound for a pharmacological agent which enhances Smad2/TGF-β receptor interaction. Preferably the Smad2 polypeptide comprises a mutation or mutations selected from the group consisting of Ser464A; Ser465A; Ser467A; Ser464A and Ser465A; Ser464A and Ser467A; Ser465A and Ser467A; Ser464A, Ser465A and Ser465A; Ser465D; Ser467D; and Ser465D and Ser467D.

According to a further aspect of the invention, methods are provided for identifying lead compounds for a pharmacological agent useful in the diagnosis or treatment of disease associated with TGF-β-mediated Smad2 signal transduction activity. The methods involve forming a mixture of a wild type Smad2 polypeptide, a TGF-β receptor, and a candidate pharmacological agent comprising a mutated Smad2 polypeptide, preferably having a mutation at one or more of serines 464, 465 and 467. The mixture is incubated under conditions which, in the absence of the candidate pharmacological agent, permit a first amount of TGF-β mediated phosphorylation of the wild type Smad2 polypeptide. A test amount of TGF-β mediated phosphorylation of the wild type Smad2 polypeptide then is detected. Detection of a reduction in the test amount of TGF-β mediated phosphorylation of the wild type Smad2 polypeptide relative to the first amount of TGF-β mediated phosphorylation of the wild type Smad2 polypeptide indicates that the candidate pharmacological agent is a lead compound for a pharmacological agent which disrupts the TGF-β mediated Smad2 signal transduction activity. Preferably the mutated Smad2 polypeptide comprises a mutation or mutations selected from the group consisting of Ser464A; Ser465A; Ser467A; Ser464A and Ser465A; Ser464A and Ser467A; Ser465A and Ser467A; Ser464A, Ser465A and Ser465A; Ser465D; Ser467D; and Ser465D and Ser467D, or TGF-β receptor binding fragments thereof.

According to another aspect of the invention, methods for determining the amount of a pathway-restricted Smad polypeptide having a phosphorylated C-terminal serine residue in a biological sample are provided. The methods include contacting the biological sample with an isolated polypeptide that selectively binds at least one phosphorylated serine of the amino acid sequence as set forth in SEQ ID NO:5, determining the binding of the isolated polypeptide to the pathway-restricted Smad polypeptide, and comparing the binding to a control as a determination of the amount of a pathway-restricted Smad polypeptide having a phosphorylated C-terminal serine residue in the biological sample. The biological sample can be a biological extract such as in vitro extract, or can be tissue sample for in vivo or in vitro immunohistochemistry analysis. In certain embodiments, the pathway-restricted Smad polypeptide is selected from the group consisting of Smad1, Smad2, Smad3, Smad5, and Smad9. In preferred embodiments, the isolated binding polypeptides include antibodies and fragments of antibodies, including monoclonal antibodies. In certain of the preferred embodiments, the antibody or antibody fragment selectively binds a pathway-restricted Smad polypeptide having at least one phosphorylated C-terminal serine residue selected from the group consisting of the second serine residue of SEQ ID NO:5, the third serine residue of SEQ ID NO:5 and the second and third serine residues of SEQ ID NO:5.

Accordig to yet another aspect of the invention, methods for identifying lead compounds for a pharmacological agent which modulate phosphorylation of the C-terminal serine residues of a pathway-restricted Smad polypeptide are provided. The methods include forming a mixture comprising a pathway-restricted Smad polypeptide having at least one C-terminal serine residue, a TGF-β superfamily receptor or receptor complex capable of phosphorylating the at least one C-terminal serine residue, and a candidate pharmacological agent. The mixture is incubated under conditions which, in the absence of the candidate pharmacological agent, permit a first amount of phosphorylation of the at least one C-terminal serine residue by the TGF-β superfamily receptor or receptor complex. A test amount of the phosphorylation of the at least one C-terminal serine residue by the TGF-β superfamily receptor or receptor complex then is detected. A reduction of the test amount of phosphorylation relative to the first amount of phosphorylation indicates that the candidate pharmacological agent is a lead compound for a pharmacological agent which reduces phosphorylation of the at least one C-terminal serine residue of a pathway-restricted Smad polypeptide. An increase of the test amount of phosphorylation relative to the first amount of phosphorylation indicates that the candidate pharmacological agent is a lead compound for a pharmacological agent which increases the phosphorylation of the C-terminal serine residues of a pathway-restricted Smad polypeptide. In certain embodiments, the pathway-restricted Smad polypeptide is selected from the group consisting of Smad1, Smad2, Smad3, Smad5, and Smad9. In other embodiments, the at least one C-terminal serine residue is selected from the group consisting of the second serine residue of SEQ ID NO:5, the third serine residue of SEQ ID NO:5 and the second and third serine residues of SEQ ID NO:5. In still other embodiments, the step of forming a mixture comprising a pathway-restricted Smad polypeptide, a TGF-β superfamily receptor or receptor complex, and a candidate pharmacological agent includes contacting a cell which includes a pathway-restricted Smad polypeptide and a TGF-β receptor or receptor complex with a candidate pharmacological agent. In preferred embodiments of the foregoing methods, the step of forming a mixture further comprises adding a ligand which activates the TGF-β superfamily receptor or receptor complex.

In another aspect of the invention methods for reducing heteromeric Smad protein complex formation in a cell is provided. The methods include providing an antibody which selectively binds a phosphorylated pathway-restricted Smad polypeptide or a nucleic acid encoding the antibody, and contacting the cell with an amount of the antibody or the nucleic acid encoding the antibody sufficient to reduce formation of the heteromeric Smad protein complex in the cell. In certain embodiments, the pathway-restricted Smad polypeptide is selected from the group consisting of Smad1, Smad2, Smad3, Smad5, and Smad9. In other embodiments, the antibody selectively binds a pathway-restricted Smad polypeptide having at least one phosphorylated C-terminal serine residue selected from the group consisting of the second serine residue of SEQ ID NO:5, the third serine residue of SEQ ID NO:5 and the second and third serine residues of SEQ ID NO:5.

Use of the foregoing compounds in the preparation of a medicament also in provided.

These and other aspects of the invention will be described in further detail in connection with the detailed description of the invention.

BRIEF DESCRIPTION OF THE SEQUENCES

Figure 1A:
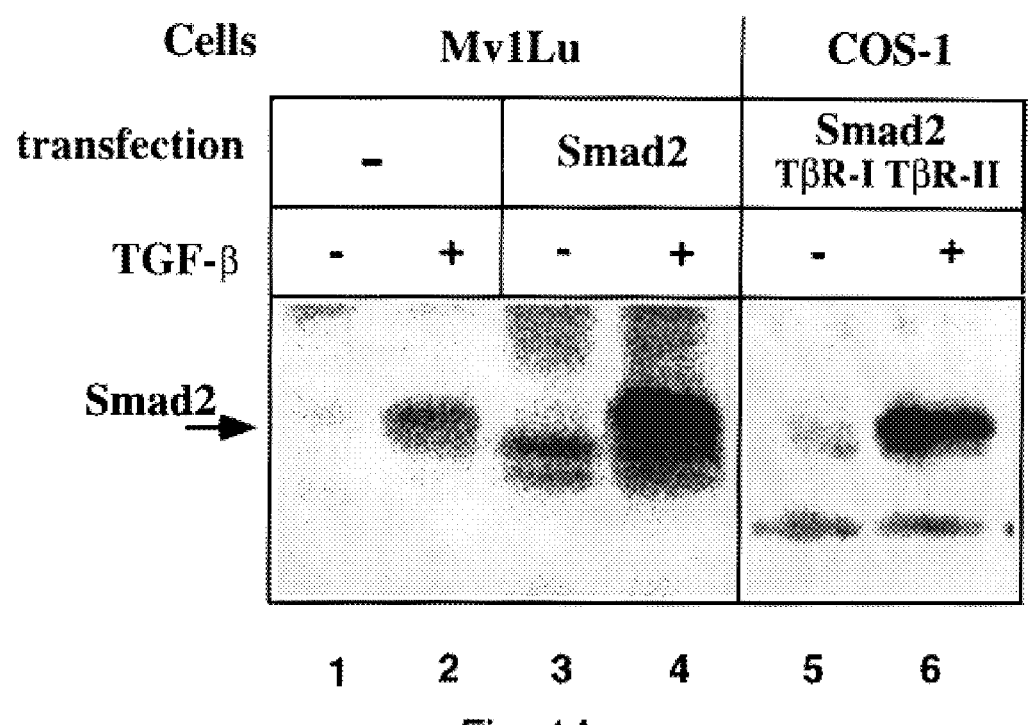
FIGS. 1A–1G depict TβR-mediated phosphorylation of Smad2.

SEQ ID NO:1 is the nucleotide sequence of the mouse Smad2 cDNA (accession number U60530).

SEQ ID NO:2 is the amino acid sequence of the mouse Smad2 protein (accession number U60530).

SEQ ID NO:3 is the amino acid sequence of the four amino acid fragment of the Smad2 C-terminus which binds Smad4.

SEQ ID NO:4 is the amino acid sequence of the fourteen amino acid fragment of the Smad2 C-terminus which binds Smad4.

SEQ ID NO:5 is the amino acid sequence of the C-terminal motif of the pathway-restricted Smads.

SEQ ID NO:6 is the amino acid sequence of a peptide used to prepare polyclonal antibodies to phosphorylated Smad2.

SEQ ID NO:7 is the amino acid sequence of another phosphorylated Smad2 peptide used for preparation of antibodies.

SEQ ID NO:8 is the amino acid sequence of the C-terminus of Smad1, Smad3, Smad5 and Smad9 proteins.

SEQ ID NO:9 is the amino acid sequence of the phosphorylated peptide used for preparation of antibodies to Smad1, Smad3, Smad5 and Smad9.

SEQ ID NO:10 is the amino acid sequence of the fourteen amino acid fragment of the Smad1 protein C-terminus.

SEQ ID NO:11 is the amino acid sequence of the fourteen amino acid fragment of the Smad3 protein C-terminus.

SEQ ID NO:12 is the amino acid sequence of the fourteen amino acid fragment of the Smad5 protein C-terminus.

SEQ ID NO:13 is the amino acid sequence of the fourteen amino acid fragment of the Smad9 protein C-terminus.

SEQ ID NO:14 is the nucleotide sequence of the human Smad2 mRNA (accession number AF027964).

SEQ ID NO:15 is the amino acid sequence of the human Smad2 protein (accession number AF027964).

DETAILED DESCRIPTION OF THE INVENTION

We present the identification of TGF-β-mediated phosphorylation of Smad2 at two serine residues in the C-terminus of the protein, i.e., Ser465 and Ser467. Phosphorylation of Ser465 required that Ser467 was phosphorylated. Mutation of Ser465 and/or Ser467 in Smad2 to alanine residues resulted in dominant negative inhibition of TGF-β signaling, as did mutation of Ser464 which is not an in vivo phosphorylation site. These Smad2 mutants were found to interact stably with an activated TGF-β receptor complex, in contrast to wild-type Smad2, which interacts only transiently. A peptide containing the four C-terminal amino acid residues of Smad2 with Ser465 and Ser467 phosphorylated, bound in vitro to a glutathione S-transferase-Smad4 fusion protein with higher affinity that the corresponding non-phosphorylated peptide. Binding to GST-Smad4 was strongly enhanced when a longer C-terminal peptide (14 amino acid residues) was used, and binding was in this case seen also in the absence of phosphorylation.

The invention thus involves in one aspect Smad2 polypeptides, genes encoding those polypeptides, functional modifications and variants of the foregoing, useful fragments of the foregoing, as well as therapeutics relating thereto. The invention also involves the recognition that pathway-restricted Smad proteins (including Smad1, Smad2, Smad3, Smad5, and Smad9) share a conserved sequence at the C-terminus (SEQ ID NO:5), and therefore the invention relates to all of the pathway-restricted Smad proteins.

The invention provides isolated polypeptides, such as variants of the Smad2 polypeptides described previously (e.g., Nakao et al., 1996; SEQ ID NO:2). In particular, mutants of the Smad2 polypeptide (e.g. the mouse protein is represented by SEQ ID NO:2) and fragments thereof are provided. Such polypeptides are useful, for example, alone for the modulation of TGF-β signal transduction or as fusion proteins to generate antibodies, e.g., for use as components of an immunoassay.

The peptides of the invention are isolated peptides. As used herein, with respect to peptides, the term "isolated peptides" means that the peptides are substantially pure and are essentially free of other substances with which they may be found in nature or in vivo systems to an extent practical and appropriate for their intended use. In particular, the peptides are sufficiently pure and are sufficiently free from other biological constituents of their hosts cells so as to be useful in, for example, producing pharmaceutical preparations or sequencing. Because an isolated peptide of the invention may be admixed with a pharmaceutically acceptable carrier in a pharmaceutical preparation, the peptide may comprise only a small percentage by weight of the preparation. The peptide is nonetheless substantially pure in that it has been substantially separated from the substances with which it may be associated in living systems.

As used herein, Smad2 polypeptides include polypeptides which contain one or more modifications to the primary amino acid sequence of Smad2 (e.g. SEQ ID NO:2), e.g. mutant "variants" of "wild-type" Smad2. Modifications which create a Smad2 mutant can be made to a Smad2 polypeptide I) to reduce or eliminate an activity of a Smad2 polypeptide, such as TGF-β receptor mediated phosphorylation; 2) to enhance a property of a Smad2 polypeptide, such as binding to TβR-I or protein stability in an expression system or the stability of protein-protein binding; or 3) to provide a novel activity or property to a Smad2 polypeptide, such as addition of an antigenic epitope or addition of a detectable moiety. Modifications to a Smad2 polypeptide are typically made to the nucleic acid which encodes the Smad2 polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the Smad2 amino acid sequence. Fragments of Smad2 which retain characteristic activities such as the TGF-β receptor binding or interaction activity, the inhibition of wild-type Smad2 activity and the ability to decrease TGF-β-mediated signaling and gene expression. One of ordinary skill in the art can readily determine which fragments retain such activities by preparing fragments of non-wild-type Smad2 using standard procedures such as PCR, restriction endonucleiase digestion, or site-directed mutagenesis, and then testing such fragments for non-wild-type Smad2 activities as described herein.

Smad2 polypeptides also include polypeptides referred to herein as "Smad4 binding polypeptides". Such Smad2 polypeptides comprise the portion of Smad 2 which binds to Smad4. As demonstrated below in the examples, Smad4 binding polypeptides can be as small as four amino acids in length, and as large as wild-type Smad2 or larger. It has been discovered that the C-terminus of Smad2 directs the binding of Smad2 to Smad4 and thus preferred examples of Smad4 binding polypeptides include the C-terminal end of Smad2. Examples include the polypeptides of SEQ ID NO:3, SEQ ID NO:4, and SEQ ID NO:5. Other Smad4 binding polypeptides which include SEQ ID NO:3 and additional amino acids of Smad2 C-terminus are contemplated. As will be apparent to one of ordinary skill in the art, Smad4 binding polypeptides also can include non-Smad amino acid sequences.

It has been discovered that the Smad4 binding polypeptide has increased activity when phosphorylated. Thus, it is preferable to prepare and use phosphorylated Smad4 binding polypeptides as exemplified below. One of ordinary skill in the art can prepare such polypeptides by using methods and materials well known in the art.

In general, mutants include pathway-restricted Smad polypeptides such as Smad2 polypeptides which are modified specifically to alter a feature of the polypeptide related to its physiological activity. For example, the experimental evidence provided below demonstrates that serines 465 and 467 are the in vivo phosphorylation sites on Smad2. It has also been demonstrated that serine 464 is important for certain Smad2 activities. Thus mutations to one or more of these serine residues can create a Smad2 polypeptide which has different activity than the wild-type Smad2. Such mutants are useful for, inter alia, modulation of TGF-β signal transduction in vitro and in vivo. Smad2 mutants can be used to modulate TGF-β activity for a variety of therapeutic and experimental uses as provided elsewhere herein. Other uses will be apparent to one of ordinary skill in the art.

As demonstrated in the examples below, substitution of alanine residues or aspartic acid residues for the aforementioned serines in Smad2 results in mutant Smad2 polypeptides with varying degrees of activity with respect to TGF-β receptor interaction, reduction of TGF-β mediated gene expression, reduction of phosphorylation of wild-type Smad2, and the like. It will be clear to one of ordinary skill in the art that other mutations can be made with equal facility using techniques which are standard in the art. Such mutations are not limited to point mutations but also embrace larger deletions and truncations.

In general, variants include Smad2 polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a Smad2 polypeptide by eliminating proteolysis by proteases in an expression system (e.g., dibasic amino acid residues in yeast expression systems in which KEX2 protease activity is present). In addition, mutations which do not result in additional altered activity can be incorporated to enable ease of detection, greater stability, or other properties at the discretion of the artisan.

Mutations of a nucleic acid which encode a pathway-restricted Smad polypeptide such as a Smad2 polypeptids preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant pathway-restricted Smad polypeptides such as Smad2 polypeptides are then expressed and tested for one or more activities to determine which mutation provides a variant polypeptide with the desired properties. Further mutations can be made to variants (or to non-variant Smad2 polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a Smad2 gene or cDNA clone to enhance expression of the polypeptide. The activity of variants of pathway-restricted Smad polypeptides such as Smad2 polypeptides can be tested by cloning the gene encoding the variant Smad polypeptide into a bacterial or mammalian expression vector, introducing the vector into an appropriate host cell, expressing the variant Smad polypeptide, and testing for a functional capability of the Smad polypeptides as disclosed herein. For example, the variant Smad2 polypeptide can be tested for inhibition of TGF-β signaling activity as disclosed in the Examples, or for inhibition of Smad2 phosphorylation or for binding to Smad4 as is also disclosed herein. Preparation of other variant polypeptides may favor testing of other activities, such as anitbody binding, as will be known to one of ordinary skill in the art.

The skilled artisan will also realize that conservative amino acid substitutions may be made in pathway-restricted Smad polypeptides such as Smad2 polypeptides to provide functionally equivalent variants of the foregoing polypeptides, i.e, the variants retain the functional capabilities of the Smad2 polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, New York, 1989, or *Current Protocols in Molecular Biology*, F. M. Ausubel, et al., eds., John Wiley & Sons, Inc., New York. Exemplary functionally equivalent variants of the Smad2 polypeptides include conservative amino acid substitutions of SEQ ID NOs:2, 3 and 4. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Conservative amino-acid substitutions in the amino acid sequence of pathway-restricted Smad polypeptides such as Smad2 polypeptides to produce functionally equivalent variants of Smad2 polypeptides typically are made by alteration of the nucleic acid encoding Smad2 polypeptides (e.g., SEQ ID NOs:2, 3 and 4). Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488–492, 1985), or by chemical synthesis of a gene encoding a Smad2 polypeptide. Where amino acid substitutions are made to a small unique fragment of a pathway-restricted Smad polypeptide (e.g. a Smad2 polypeptide), such as a Smad4 binding polypeptide, the substitutions can be made by directly synthesizing the peptide. The activity of functionally equivalent fragments of Smad2 polypeptides can be tested by cloning the gene encoding the altered Smad2 polypeptide into a bacterial or mammalian expression vector, introducing the vector into an appropriate host cell, expressing the altered Smad2 polypeptide, and testing for a functional capability of the Smad2 polypeptides as disclosed herein. Peptides which are chemically synthesized can be tested directly for function, e.g., for binding to Smad4.

Homologs and alleles of the Smad2 nucleic acids of the invention can be identified by conventional techniques. Thus, an aspect of the invention is those nucleic acid sequences which code for Smad2 polypeptides and which hybridize to a nucleic acid molecule consisting of the coding region of SEQ ID NO:1 or SEQ ID NO:14, under stringent conditions. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, New York, 1989, or *Current Protocols in Molecular*

*Biology*, F. M. Ausubel, et al., eds., John Wiley & Sons, Inc., New York. More specifically, stringent conditions, as used herein, refers, for example, to hybridization at 65° C. in hybridization buffer (3.5× SSC, 0.02% Ficoll, 0.02% polyvinyl pyrolidone, 0.02% Bovine Serum Albumin, 2.5mM NaH$_2$PO$_4$(pH7), 0.5% SDS, 2mM EDTA). SSC is 0.15M sodium chloride/0.15M sodium citrate, pH7; SDS is sodium dodecyl sulphate; and EDTA is ethylenediaminetetracetic acid. After hybridization, the membrane upon which the DNA is transferred is washed at 2× SSC at room temperature and then at 0.1× SSC/0.1× SDS at temperatures up to 65° C.

There are other conditions, reagents, and so forth which can used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of Smad2 nucleic acids of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 40% nucleotide identity and/or at least 50% amino acid identity to SEQ ID NO:1 and SEQ ID NO:2 (or SEQ ID NO:14 and SEQ ID NO:15), respectively, in some instances will share at least 50% nucleotide identity and/or at least 65% amino acid identity and in still other instances will share at least 60% nucleotide identity and/or at least 75% amino acid identity. Watson-Crick complements of the foregoing nucleic acids also are embraced by the invention.

In screening for Smad2 nucleic acids, a Southern blot may be performed using the foregoing conditions, together with a radioactive probe. After washing the membrane to which the DNA is finally transferred, the membrane can be placed against X-ray film to detect the radioactive signal. The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating Smad2 polypeptide. Similarly, nucleotide sequence triplets which encode other amino acid residues include, but are not limited to: CCA, CCC, CCG and CCT (proline codons); CGA, CGC, CCG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

In one set of embodiments, the nucleic acids of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These nucleic acids may be prepared by art recognized methods which may be carried out manually or by an automated synthesizer. They also may be produced recombinantly by vectors.

In preferred embodiments, however, the nucleic acids of the invention also may include "modified" oligonucleotides. That is, the nucleic acids may be modified in a number of ways which do not prevent their transcription or translation but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified nucleic acids that encode Smad2 polypeptides, together with pharmaceutically acceptable carriers.

Nucleic acids encoding the pathway-restricted Smad polypeptides such as Smad2 polypeptides of the invention (including TGF-β receptor binding and Smad4 binding polypeptides) may be administered as part of a pharmaceutical composition. Such a pharmaceutical composition may include the nucleic acids in combination with any standard physiologically and/or pharmaceutically acceptable carriers which are known in the art. The compositions should be sterile and contain a therapeutically effective amount of the nucleic acids in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual,* Second Edition, Cold Spring Harbor Laboratory Press, 1989. Cells are genetically engineered by the introduction into the cells of heterologous DNA (RNA) encoding Smad2 polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata *(Nuc. Acids Res.* 25 18:5322, 1990), and its use in transfection experiments is disclosed by, for example, Demoulin *(Mol. Cell. Biol.* 16:4710–4716, 1996). Still another preferred expression vector is an adenovirus, described by Stratford-Perricaudet, which is defective for E1 and E3 proteins *(J. Clin. Invest.* 90:626–630, 1992). The use of the adenovirus as an Adeno. P1A recombinant is disclosed by Warnier et al., in intradermal injection in mice for immunization against P1A *(Int. J. Cancer,* 67:303–310, 1996).

The invention also embraces so-called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

The invention also permits the construction of Smad2 mutant gene "transgenics" in cells and in animals, providing materials for studying certain aspects of TGF-β signal transduction.

The invention as described herein has a number of uses, some of which are described elsewhere herein. First, the invention permits preparation and isolation of the Smad2 polypeptides with non-wild-type activities such as reduced or even ablated phosphorylation. A variety of methodologies well-known to the skilled practitioner can be utilized to obtain isolated Smad2 molecules. The polypeptide may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of mRNA in cell-free extracts such as the reticulocyte lysate system also may be used to produce polypeptide. Those skilled in the art also can readily follow known methods for isolating Smad2 polypeptides. These include, but are not limited to, immunochromotography, HPLC, size-exclusion chromatography, ion-exchange chromatography and immune-affinity chromatography.

The identification of the in vivo phosphorylation sites and Smad4 binding interface of pathway-restricted Smad polypeptides such as Smad2 polypeptides also makes it possible for the artisan to diagnose and modulate disorders characterized by aberrant TGF-β signaling activity. These methods involve in certain embodiments contacting the Smad polypeptides of the invention to cells suspected of having elevated TGF-β signaling. The Smad polypeptides of the invention act as dominant-negative inhibitors of TGF-β mediated phosphorylation of wild-type Smad and binding of pathway-restricted Smad polypeptides such as Smad2 polypeptides and Smad4 and thus can modulate elevated TGF-β signaling.

The invention also makes it possible isolate proteins such as TβR-I and Smad4 by the binding of such proteins to pathway-restricted Smad polypeptides such as Smad2 polypeptides as disclosed herein. The identification of this binding also permits one of skill in the art to block the binding of pathway-restricted Smad polypeptides such as Smad2 polypeptides to other proteins, such as TβR-I and Smad4. Binding of the proteins can be effected by introducing into a biological system in which the proteins bind (e.g., a cell) a polypeptide including a Smad TβR-I binding site in an amount sufficient to block the binding. The identification of a Smad4 binding site in Smad2 also enables one of skill in the art to prepare modified proteins, using standard recombinant DNA techniques, which can bind to proteins such as Smad4.

The invention further provides methods for reducing or increasing TGF-β signal transduction in a cell. Such methods are useful in vitro for altering the TGF-β signal transduction, for example, in testing compounds for potential to block aberrant TGF-β signal transduction or increase deficient TGF-β signal transduction. In vivo, such methods are useful for modulating growth, e.g., to treat cancer. Increasing TGF-β signal transduction in a cell by, e.g., introducing a dominant negative Smad2 polypeptide in the cell, can be used to provide a model system for testing the effects of putative inhibitors of TGF-β signal transduction. Such methods also are useful in the treatment of conditions which result from excessive or deficient TGF-β signal transduction. TGF-β signal transduction can be measured by a variety of ways known to one of ordinary skill in the art, such as the reporter systems described in the Examples. Various modulators of the activity of pathway-restricted Smad polypeptides such as Smad2 can be screened for effects on TGF-β signal transduction using the methods disclosed herein. The skilled artisan can first determine the modulation of a Smad2 activity, such as TGF-β signaling activity, and then apply such a modulator to a target cell or subject and assess the effect on the target cell or subject. For example, in screening for modulators of Smad2 useful in the treatment of cancer, cells in culture can be contacted with Smad2 modulators and the increase or decrease of growth or focus formation of the cells can be determined according to standard procedures. Smad2 activity modulators can be assessed for their effects on other TGF-β signal transduction downstream effects by similar methods in many cell types.

The invention also provides, as previously noted, "dominant negative" polypeptides derived from Smad2. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to a promoter site in the control region of a gene but does not increase gene transcription can reduce the effect of a normal transcription factor by occupying promoter binding sites without increasing transcription.

The end result of the expression of a dominant negative polypeptide in a cell is a reduction in function of active proteins. One of ordinary skill in the art can assess the potential for a dominant negative variant of a protein, and using standard mutagenesis techniques to create one or more dominant negative variant polypeptides. For example, given the teachings contained herein of mutant Smad2 polypeptides, one of ordinary skill in the art can modify the sequence of the Smad2 polypeptide (SEQ ID NO:2) by site-specific mutagenesis, scanning mutagenesis, partial gene deletion or truncation of the Smad2 cDNA, and the like. See, e.g., U.S. Pat. No. 5,580,723 and Sambrook et al., *Molecular Cloning: A Laboratory Manual,* Second Edition, Cold Spring Harbor Laboratory Press, 1989. The skilled artisan then can test the population of mutagenized polypeptides for diminution in a selected activity and/or for retention of such an activity (e.g., Smad2 reduction of TGF-β signaling activity). Other similar methods for creating and testing dominant negative variants of a protein will be apparent to one of ordinary skill in the art.

Dominant negative pathway-restricted Smad polypeptides (e.g., Smad2 polypeptides) include variants in which the in vivo phosphorylation sites are mutated or in which a portion of the Smad4 binding site has been mutated or deleted to reduce or eliminate Smad2 interaction with the Smad4. One of ordinary skill in the art can readily prepare and test Smad2 mutant and variants bearing mutations or deletions for diminution of selected activities.

The invention also involves agents such as polypeptides which bind to pathway-restricted Smad polypeptides such as the Smad2 polypeptides of the invention and to complexes of Smad polypeptides and binding partners such as TβR-I or Smad4. Such binding agents can be used, for example, in screening assays to detect the presence or absence of Smad polypeptides and complexes of Smad polypeptides and their binding partners and in purification protocols to isolate Smad polypeptides and complexes of Smad polypeptides and their binding partners. Such agents also can be used to inhibit the native activity of the Smad polypeptides or their binding partners, for example, by binding to such polypeptides, or their binding partners or both.

The invention, therefore, embraces peptide binding agents which, for example, can be antibodies or fragments of antibodies having the ability to selectively bind to Smad2 polypeptides of the invention. Antibodies include polyclonal and monoclonal antibodies, prepared according to conventional methodology (e.g., Kohler and Milstein, *Nature,* 256:495, 1975). As exemplified below, preferred antibodies include antibodies which bind selectively to the phosphorylated tail of Smad2 (Smad2 phospho tail antibodies). Other preferred antibodies include similar phospho tail-specific antibodies for other pathway-restricted Smad proteins (e.g. Smad1, Smad3, Smad5, Smad9). Included in the foregoing are antibodies raised against the four amino acid C-terminal motif of pathway-restricted Smads (SEQ ID NO:5), and antibodies raised against longer phosphorylated fragments of Smad proteins which recognized individual Smad proteins (e.g. SEQ ID NO:4 and corresponding sequences in other pathway-restricted Smads).

An "antibody" as used herein includes human monoclonal antibodies or functionally active fragments thereof having human constant regions and a Smad protein binding CDR3 region from a mammal of a species other than a human.

Significantly, as is well-known in the art, only a small portion of an antibody molecule, the paratope, is involved in the binding of the antibody to its epitope (see, in general, Clark, W. R. (1986) *The Experimental Foundations of Modem Immunology* Wiley & Sons, Inc., New York; Roitt, I. (1991) *Essential Immunology,* 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies. Humanized monoclonal antibodies may be made by any method known in the art.

Humanized monoclonal antibodies, for example, may be constructed by replacing the non-CDR regions of a non-human mammalian antibody with similar regions of human antibodies while retaining the epitopic specificity of the original antibody. For example, non-human CDRs and optionally some of the framework regions may be covalently joined to human FR and/or Fc/pFc' regions to produce a functional antibody. There are entities in the United States which will synthesize humanized antibodies from specific murine antibody regions commercially, such as Protein Design Labs (Mountain View Calif.).

European Patent Application 0239400, the entire contents of which is hereby incorporated by reference, provides an exemplary teaching of the production and use of humanized monoclonal antibodies in which at least the CDR portion of a murine (or other non-human mammal) antibody is included in the humanized antibody. Briefly, the following methods are useful for constructing a humanized CDR monoclonal antibody including at least a portion of a mouse CDR. A first replicable expression vector including a suitable promoter operably linked to a DNA sequence encoding at least a variable domain of an Ig heavy or light chain and the variable domain comprising framework regions from a human antibody and a CDR region of a murine antibody is prepared. Optionally a second replicable expression vector is prepared which includes a suitable promoter operably linked to a DNA sequence encoding at least the variable domain of a complementary human Ig light or heavy chain respectively. A cell line is then transformed with the vectors. Preferably the cell line is an immortalized mammalian cell line of lymphoid origin, such as a myeloma, hybridoma, trioma, or quadroma cell line, or is a normal lymphoid cell which has been immortalized by transformation with a virus. The transformed cell line is then cultured under conditions known to those of skill in the art to produce the humanized antibody.

As set forth in European Patent Application 0239400 several techniques are well known in the art for creating the particular antibody domains to be inserted into the replicable vector. For example, the DNA sequence encoding the domain may be prepared by oligonucleotide synthesis. Alternatively a synthetic gene lacking the CDR regions in which four framework regions are fused together with suitable restriction sites at the junctions, such that double stranded synthetic or restricted subcloned CDR cassettes with sticky ends could be ligated at the junctions of the framework regions. Another method involves the preparation of the DNA sequence encoding the variable CDR containing domain by oligonucleotide site-directed mutagenesis. Each of these methods is well known in the art. Therefore, those skilled in the art may construct humanized antibodies containing a murine CDR region without destroying the specificity of the antibody for its epitope.

In preferred embodiments, the humanized antibodies of the invention are human monoclonal antibodies including at least the Smad protein binding CDR3 region of the deposited monoclonal antibody. As noted above, such humanized antibodies may be produced in which some or all of the FR regions of deposited monoclonal antibody have been replaced by homologous human FR regions. In addition, the Fe portions may be replaced so as to produce IgA or IgM as well as human IgG antibodies bearing some or all of the CDRs of the Smad phospho tail antibodies. Of particular importance is the inclusion of the Smad phospho tail protein binding CDR3 region and, to a lesser extent, the other CDRs and portions of the framework regions of the Smad phospho tail antibodies. Such humanized antibodies will have particular clinical utility in that they will specifically recognize Smad proteins, particularly phosphorylated forms, but will not evoke an immune response in humans against the antibody itself.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences.

As used herein the term "functionally active antibody fragment" means a fragment of an antibody molecule including a Smad protein binding region of the invention which retains the Smad binding functionality of an intact antibody having the same specificity as the antibodies disclosed herein. Such fragments are also well known in the art and are regularly employed both in vitro and in vivo. In particular, well-known functionally active antibody fragments include but are not limited to F(ab')$_2$, Fab, Fv and Fd fragments of antibodies. These fragments which lack the Fc fragment of intact antibody, clear more rapidly from the circulation, and may have less non-specific tissue binding than an intact antibody (Wahl et al., *J. Nucl. Med.* 24:316–325 (1983)). For example, single-chain antibodies can be constructed in accordance with the methods described in U.S. Pat. No. 4,946,778 to Ladner et al. Such single-chain antibodies include the variable regions of the light and heavy chains joined by a flexible linker moiety. Methods for obtaining a single domain antibody ("Fd") which comprises an isolated variable heavy chain single domain, also have been reported (see, for example, Ward et al., *Nature* 341:644–646 (1989), disclosing a method of screening to identify an antibody heavy chain variable region (V. single domain antibody) with sufficient affinity for its target epitope to bind thereto in isolated form). Methods for making recombinant Fv fragments based on known antibody heavy chain and light chain variable region sequences are known in the art and have been described, e.g., Moore et al., U.S. Pat. No. 4,462,334. Other references describing the use and generation of antibody fragments include e.g., Fab fragments (Tijssen, Practice and Theory of Enzyme Immunoassays (Elsevier, Amsterdam, 1985)), Fv fragments (Hochman et al., *Biochemistry* 12: 1130 (1973); Sharon et al., *Biochemistry* 15: 1591 (1976); Ehrilch et al., U.S. Pat. No. 4,355,023) and portions of antibody molecules (Audilore-Hargreaves, U.S. Pat. No. 4,470,925). Thus, those skilled in the art may construct antibody fragments from various portions of intact antibodies without destroying the specificity of the antibodies for the Smad protein epitope.

Functionally active antibody fragments also encompass "humanized antibody fragments." As one skilled in the art will recognize, such fragments could be prepared by traditional enzymatic cleavage of intact humanized antibodies. If, however, intact antibodies are not susceptible to such cleavage, because of the nature of the construction involved, the noted constructions can be prepared with immunoglobulin fragments used as the starting materials; or, if recombinant techniques are used, the DNA sequences, themselves, can be tailored to encode the desired "fragment" which, when expressed, can be combined in vivo or in vitro, by chemical or biological means, to prepare the final desired intact immunoglobulin fragment.

Thus, the invention in certain aspects involves polypeptides of numerous size and type that bind specifically to pathway-restricted Smad polypeptides (including Smad4 binding polypeptides), and complexes of Smad polypeptides and their binding partners. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention, e.g. those which bind to phosphorylated portions of pathway restricted Smad polypeptides, particularly the C-terminal amino acid motif set forth in SEQ ID NO:5, with or without additional amino acids to confer additional specificity to antibody binding. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the Smad2 polypeptide, e.g. having one or more phosphorylated serines in the C-terminal tail, or other similarly phosphorylated pathway-restricted Smad polypeptides. This process can be repeated through several cycles of reselection of phage that bind to the Smad polypeptide. Repeated rounds lead to enrichment of phage bearing particular sequences. DNA sequence analysis can be conducted to identify the sequences of the expressed polypeptides. The minimal linear portion of the sequence that binds to the Smad polypeptide can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the Smad polypeptides. Thus, the Smad2 polypeptides of the invention, other phosphorylated pathway-restricted Smads and fragments thereof, can be used to screen peptide libraries, including phage display libraries, to identify and select peptide binding partners of the Smad polypeptides of the invention. Such molecules can be used, as described, for screening assays, for purification protocols, for interfering directly with the functioning of Smad polypeptides and for other purposes that will be apparent to those of ordinary skill in the art.

A Smad2 polypeptide, or a fragment thereof, also can be used to isolate the native binding partners, including, e.g., the TGF-β receptor complex and Smad4. Isolation of such binding partners may be performed according to well-known methods. For example, isolated Smad2 polypeptides can be attached to a substrate (e.g., chromatographic media, such as polystyrene beads, or a filter), and then a solution suspected of containing the TGF-β receptor complex may be applied to the substrate. If a TGF-β receptor complex which can interact with Smad2 polypeptides is present in the solution, then it will bind to the substrate-bound Smad2 polypeptide. The TGF-β receptor complex then may be isolated. Other proteins which are binding partners for Smad2, such as other Smads or activin receptor complexes, may be isolated by similar methods without undue experimentation.

It will also be recognized that the invention embraces the use of the Smad2 cDNA sequences in expression vectors, as well as to transfect host cells and cell lines, be these prokaryotic (e.g., *E. coli*), or eukaryotic (e.g., CHO cells, COS cells, yeast expression systems and recombinant baculovirus expression in insect cells). Especially useful are mammalian cells such as human, mouse, hamster, pig, goat, primate, etc. They may be of a wide variety of tissue types, and include primary cells and cell lines. Specific examples include keratinocytes, peripheral blood leukocytes, bone marrow stem cells and embryonic stem cells. The expression vectors require that the pertinent sequence, i.e., those nucleic acids described supra, be operably linked to a promoter.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The therapeutics of the invention can be administered by any conventional route, including injection or by gradual infusion over time. The administration may, for example, be oral, intravenous, intraperitoneal, intramuscular, intracavity, subcutaneous, or transdermal. When antibodies are used therapeutically, a preferred route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences,* 18th edition, 1990, pp 1694–1712; incorporated by reference). Those of skill in the art can readily determine the various parameters and conditions for producing antibody aerosols without resort to undue experimentation. When using antisense preparations of the invention, slow intravenous administration is preferred.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The preparations of the invention are administered in effective amounts. An effective amount is that amount of a pharmaceutical preparation that alone, or together with further doses, produces the desired response. In the case of treating cancer, the desired response is inhibiting the progression of the cancer. This may involve only slowing the progression of the disease temporarily, although more preferably, it involves halting the progression of the disease permanently. This can be monitored by routine methods or can be monitored according to diagnostic methods of the invention discussed herein.

The invention also contemplates gene therapy. The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy using vectors such as adenovirus, retroviruses, herpes virus, and targeted liposomes also is contemplated according to the invention.

The invention further provides efficient methods of identifying pharmacological agents or lead compounds for agents active at the level of a cellular function modulatable by apathway-restricted Smad polypeptide or fragment such as a Smad2 polypeptide or fragment thereof. In particular, such functions include TGF-β superfamily signal transduction and formation of TGF-β superfamily receptor-Smad2 and Smad2-Smad4 protein complexes. Generally, the screening methods involve assaying for compounds which interfere with a Smad activity such as TGF-β superfamily receptor-Smad binding, etc. Such methods are adaptable to automated, high throughput screening of compounds. The target therapeutic indications for pharmacological agents detected by the screening methods are limited only in that the target cellular function be subject to modulation by alteration of the formation of a complex comprising a pathway-restricted Smad polypeptide such as a Smad2 polypeptide of the invention or fragment thereof and one or more natural Smad intracellular binding targets, such as a TGF-β superfamily receptor. Target indications include cellular processes modulated by TGF-0, BMP and/or activin signal transduction following receptor-ligand binding.

A wide variety of assays for pharmacological agents are provided, including, labeled in vitro protein-protein binding assays, electrophoretic mobility shift assays, immunoassays, cell-based assays such as two- or three-hybrid screens, expression assays, etc. For example, three-hybrid screens are used to rapidly examine the effect of transfected nucleic acids on the intracellular binding of pathway-restricted Smad or Smad fragments to specific intracellular targets. The transfected nucleic acids can encode, for example, combinatorial peptide libraries or antisense molecules. Convenient reagents for such assays, e.g., GAL4 fusion proteins, are known in the art. An exemplary cell-based assay involves transfecting a cell with a nucleic acid encoding a Smad2 polypeptide fused to a GAL4 DNA binding domain and a nucleic acid encoding a Smad4 domain which interacts with Smad2 fused to a transcription activation domain such as VP16. The cell also contains a reporter gene operably linked to a gene expression regulatory region, such as one or more GAL4 binding sites. Activation of reporter gene transcription occurs when the Smad2 and Smad4 fusion polypeptides bind such that the GAL4 DNA binding domain and the VP16 transcriptional activation domain are brought into proximity to enable transcription of the reporter gene. Agents which modulate a Smad2 polypeptide mediated cell function are then detected through a change in the expression of reporter gene. Methods for determining changes in the expression of a reporter gene are known in the art.

Pathway-restricted Smad fragments used in the methods, when not produced by a transfected nucleic acid are added to an assay mixture as an isolated polypeptide. Pathway-restricted Smad polypeptides such as Smad2 polypeptides preferably are produced recombinantly, although such polypeptides may be isolated from biological extracts. Recombinantly produced Smad polypeptides include chimeric proteins comprising a fusion of a Smad protein with another polypeptide, e.g., a polypeptide capable of providing or enhancing protein-protein binding, sequence specific nucleic acid binding (such as GAL4), enhancing stability of the Smad polypeptide under assay conditions, or providing a detectable moiety, such as green fluorescent protein or Flag epitope as provided in the examples below.

The assay mixture is comprised of a natural intracellular Smad binding target such as a TGF-β superfamily receptor or fragment thereof capable of interacting with a Smad polypeptide. While natural Smad binding targets may be used, it is frequently preferred to use portions (e.g., peptides or nucleic acid fragments) or analogs (i.e., agents which mimic the Smad binding properties of the natural binding target for purposes of the assay) of the Smad binding target so long as the portion or analog provides binding affinity and avidity to the Smad fragment measurable in the assay.

The assay mixture also comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate agents encompass numerous chemical classes, although typically they are organic compounds. Preferably, the candidate pharmacological agents are small organic compounds, i.e., those having a molecular weight of more than 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids as defined herein are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily be modified through conventional chemical, physical, and biochemical means. Further, known pharmacological agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease, inhibitors, nuclease inhibitors, anti-microbial agents, and the like may also be used.

The mixture of the foregoing assay materials is incubated under conditions whereby, but for the presence of the candidate pharmacological agent, the Smad2 polypeptide specifically binds the cellular binding target, a portion thereof or analog thereof. The order of addition of components, incubation temperature, time of incubation, and other perimeters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours.

After incubation, the presence or absence of specific binding between the Smad2 polypeptide and one or more binding targets is detected by any convenient method available to the user. For cell free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximum signal to noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromotograpic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Detection may be effected in any convenient way for cell-based assays such as two- or three-hybrid screens. The transcript resulting from a reporter gene transcription assay of Smad2 polypeptide interacting with a target molecule typically encodes a directly or indirectly detectable product, e.g., β-galactosidase activity, luciferase activity, and the like. For cell free binding assays, one of the components usually comprises, or is coupled to, a detectable label. A wide variety of labels can be used, such as those that provide direct detection (e.g., radioactivity, luminescence, optical or electron density, etc). or indirect detection (e.g., epitope tag such as the FLAG epitope, enzyme tag such as horseseradish peroxidase, etc.). The label may be bound to a Smad binding partner, or incorporated into the structure of the binding partner.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, strepavidin-biotin conjugates, etc. Methods for detecting the labels are well known in the art.

The invention provides Smad-specific binding agents, methods of identifying and making such agents, and their use in diagnosis, therapy and pharmaceutical development. For example, Smad2-specific pharmacological agents are useful in a variety of diagnostic and therapeutic applications, especially where disease or disease prognosis is associated with improper utilization of a pathway involving Smad2, e.g., TGF-β induced phosphorylation of Smad2, Smad4-Smad2 complex formation, etc. Novel Smad-specific binding agents include pathway restricted Smad-specific antibodies (e.g. phospho tail antibodies) and other natural intracellular binding agents identified with assays such as two hybrid screens, and non-natural intracellular binding agents identified in screens of chemical libraries and the like.

In general, the specificity of Smad2 binding to a binding agent is shown by binding equilibrium constants. Targets which are capable of selectively binding a Smad polypeptide preferably have binding equilibrium constants of at least about $10^7$ $M^{-1}$, more preferably at least about $10^8$ $M^{-1}$, and most preferably at least about $10^9$ $M^{-1}$. The wide variety of cell based and cell free assays may be used to demonstrate pathway-restricted Smad-specific binding. Cell based assays include one, two and three hybrid screens, assays in which Smad-mediated transcription is inhibited or increased, etc. Cell free assays include Smad-protein binding assays, immunoassays, etc. Other assays useful for screening agents which bind pathway-restricted Smad polypeptides such as Smad2 polypeptides include fluorescence resonance energy transfer (FRET), and electrophoretic mobility shift analysis (EMSA).

Various techniques may be employed for introducing nucleic acids of the invention into cells, depending on whether the nucleic acids are introduced in vitro or in vivo in a host. Such techniques include transfection of nucleic acid-$CaPO_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

EXAMPLES

Materials and Methods

Cell lines

COS-1 cells and mink lung epithelial (MvlLu) cells were obtained from American Type Culture Collection. Cells were cultured in DMEM (GIBCO-BRL) with 10% fetal bovine serum, 100 units/ml of penicillin and 50 µg/ml of streptomycin.

Constructs and cell transfection

Expression of plasmids for TβR-I, TβR-II and Smad2 were previously described (ten Dijke et al., Science, 264:101–104, 1994; Nakao et al., 1996). Smad2 mutants were made by a polymerase chain reaction (PCR)-directed approach and subcloned in pcDNA3 vector. Mutations and sequences of the exchanged restriction fragments in Smad2 cDNA were confirmed by DNA sequencing. Transient transfections were performed using a DEAE-dextran protocol, as described (Cárcamo et al., Mol. Cell. Biol., 14:3810–3821, 1994).

[$^{32}$P]orthophosphate labeling, tryptic phosphopeptide mapping, two-dimensional phosphoamino acid analysis and automated Edman degradation

[$^{32}$P]orthophosphate labeling, tryptic phosphopeptide mapping, two-dimensional phosphoamino acid analysis and automated Edman degradation were performed as previously described (Souchelnytskyi et al., EMBO J, 15:6231–6240, 1996). In brief, subconfluent cells were labeled in phosphate-free medium containing 0.5% dialyzed FCS, 20 mM HEPES, pH 7.2, and [$^{32}$P]orthophosphate (1.0 mCi/ml). After stimulation with TGF-β1 for 60 min, the cells were washed and lysed in lysis buffer (20 mM Tris-HCl, pH7.4, 150 mM NaCl, 0.5% Triton X-100, 5 mM NaF, 10 mM $Na_4P_2O_7$, 1 mM $Na_3VO_4$, 1 mM phenylmethylsulphonyl fluoride (PMSF), 100 U/ml aprotinin). The cell lysates were subjected to immunoprecipitation using the SED antisera against Smad2 (SED; Nakao et al., 1996); immunoprecipitates were then subjected to SDS-PAGE and transferred to a nitrocellulose membrane. The phosphorylated Smad2 proteins were excised from the filter and digested in situ with trypsin (modified sequencing grade; Promega). Two-dimensional phosphopeptide mapping was done using the Hunter thin-layer electrophoresis (HTLE-7000; CBS Scientific), essentially as described by Boyle et al. (Methods Enzymol., 201:110–149, 1991). First dimension electrophoresis was performed in pH 1.9 buffer (formic acid/glacial acid/water; 44:156:1800; v/v/v) for 27 min at 2000 V, and chromatography in the second dimension in isobutyric acid/n-butanol/pyridine/glacial acetic acid/water (1250:38:96:58: 558; v/v/v/v/v). After exposure, phosphopeptides were eluted from the plates in pH 1.9 buffer and lyophilized; aliquots of the samples were then subjected to two-dimensional phosphoamino acid analysis and automated Edman degradation in parallel. For radiochemical sequencing, the eluted phosphopeptides were coupled to Sequelon-AA membrane (Millipore) by use of carbodiimide coupling, according to standard procedures as described by the manufacturer, and Edman degradation was performed using an Applied Biosystems sequencer (Model 477A). Released phenylthiohydantoin amino acid-derivatives from each cycle were spotted onto thin-layer chromatography plates. The radioactivity in each spot was quantitated by exposure on a FujiX Bio-Imager.

Iodination of TGF-β1 and affinity cross-linking

TGF-β1 was iodinated using the chloramine T method according to Frolik et al. (J. Biol. Chem., 259:10995–11000, 1984). Cross-linking was performed as previously described (Franzén et al., Cell, 75:681–692, 1993). Complexes of Smad2 and TGF-β receptors, cross-linked with $^{125}$I-TGF-β, were immunoprecipitated with Smad2 antiserum (SED; Nakao et al., 1996) and subjected to SDS-PAGE. Gels were dried and exposed on a FujiX Bio-Imager. To determine equality of TPR's expression, aliquots of cell lysates were subjected to immunoprecipitation using anti-TβR-I antibodies, and analyzed by SDS-PAGE and autoradiography as previously described (Franzen et al., 1993). To determine the expression of Smad proteins, cell lysates were separated by SDS-PAGE, electrotransferred to nitrocellulose membrane, immunoblotted with the Smad2 antiserum and developed using an enhanced chemiluminescence detection system (Amersham).

Transcriptional response assay

MvlLu cells were transiently transfected with p3TP-Lux (Cárcamo et al., Mol. Cell. Biol., 15:1573–1581, 1995) in the absence or presence of Smad2 expression plasmids by using the DEAE-dextran method. After transfection cells were incubated for 24 h in DMEM with 10% FBS, and then incubated with 0.1% FBS for 5 h, after which TGF-β1 was added. Luciferase activity in the cell lysate was measured after 22–24 h using the luciferase assay system (Promega Biotech), according to the manufacturer's protocol using an LKB Luminometer (LKB Bromma).

Peptide synthesis and coupling to solid support

The peptides KKKSSMS (SEQ ID NO:6) and KKKYTQMGSPSVRCSSMS (SEQ ID NO:7) were synthesized using an Applied Biosystems peptide synthesizer (model ABI 430A) by Fmoc chemistry. The corresponding peptides with the two most C-terminal serine residues phosphorylated were synthesized using phosphorylated F-moc serine residue derivatives during synthesis. The peptides were analyzed by plasma desorption mass spectrometry using an Applied Biosystems Bio Ion 20 instrument. Peptide fractions were freeze-dried and stored under dry conditions. Peptides were coupled to activated CNBr Sepharose 4B (Pharmacia) through primary amino groups according to the manufacturer's protocol; the three lysines at the N-terminus were included to facilitate efficient coupling. The efficiency of coupling was determined by measuring the $OD_{280}$ (or $OD_{215}$ for short peptides) of the peptide solution before and after coupling. The coupling efficiencies of all four peptides were nearly 100%.

Preparation of GST-fusion proteins cDNA for Smads were cloned into pGEX vectors (Pharmacia LKB), and fusion proteins were prepared and absorbed essentially as described (Smith and Johnson, *Gene*, 63:31–40, 1988).

Association of phosphorylated and nonphosphorylated Smad2 peptides with GST fusion proteins Phosphorylated and nonphosphorylated Smad2-derived C-terminal peptides were incubated with GST-Smad fusion proteins in phosphate buffered saline containing 1% Triton (PBS-T) with 0.1% BSA overnight at 4° C. After washing five times with PBS-T with 0.1% BSA and twice with PBS-T, the samples were subjected to SDS-PAGE. Proteins were electrotransferred to nitrocellulose membrane and immunoblotted with GST antiserum (gift from Aino Ruusala) and developed using an enhanced chemiluminescence detection system (Amersham).

Example 1

Mapping of in vivo phosphorylation sites in Smad2

TGF-β receptor activation leads to phosphorylation of Smad2 on serine and threonine residues (Eppert et al., 1996; Macías-Silva et al., 1996; Nakao et al., 1996). In order to localize the phosphorylated residues in Smad2, two-dimensional tryptic phosphopeptide mapping was performed. Untransfected MvlLu cells, MvlLu cells transiently transfected with Smad2 alone, and COS-1 cells transiently transfected with Smad2 together with TβR-I and TβR-II, were labeled with [$^{32}$P]orthophosphate and incubated with or without TGF-β1. Thereafter, cell lysates were subjected to immunoprecipitation using a Smad2 antiserum, followed by SDS-PAGE and autoradiography. Plates were exposed and analyzed by using a FujiX Bio-Imager. Sample application points are shown by small black squares. In the absence of TGF-β1, Smad2 was only phosphorylated at low stoichiometry; phosphorylation was dramatically enhanced after ligand-stimulation (FIG. 1A).

Figure 1B:
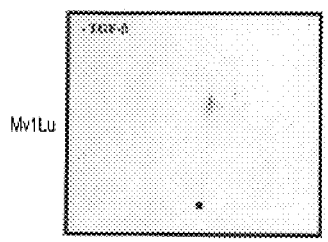
Figure 1C:
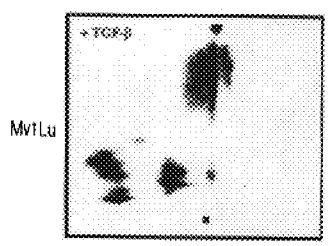
Figure 1D:
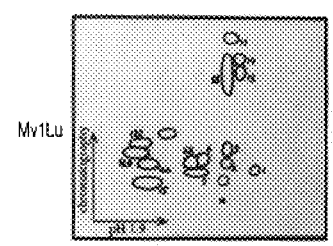

The Smad2 phosphoproteins of the experiment shown in FIG. 1A were transferred to a membrane, cut out (from lanes 3(B), 4(C), 5(E) and 6(F)) and subjected to tryptic digestion. After digestion with trypsin, peptides were resolved by high-voltage electrophoresis and thin-layer chromatography. Analysis of the two-dimensional maps of $^{32}$P-labeled phosphopeptides revealed about 16 spots of different intensities (FIGS. 1B, C, D). In the absence of ligand-stimulation, a broad smear (spot 18) and few faint spots were seen. The abundantly phosphorylated peptide (spot 18) was immunoprecipitated with antiserum raised against a peptide from a sequence in a large tryptic peptide that covers almost completely the proline-rich linker sequence between the MH1 and MH2 domains. This phosphopeptide contained phosphoserine as well as phosphothreonine.

Figure 1E:
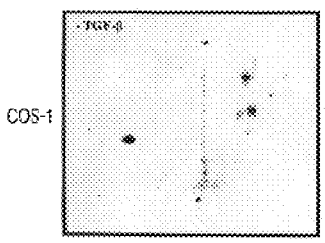

Stimulation by TGF-β1 led to the appearance and induction of multiple spots; in particular, seven highly negatively charged phosphopeptides were seen (spots 5, 6, 6n, 12a, 12b, 12c and 15). Phosphopeptide maps of endogenous and overexpressed Smad2 in MvlLu cells were identical, albeit signal intensity was higher on maps of overexpressed Smad2. Overexpression of Smad2 with TβR-I and TβR-II in COS-1 cells and incubation with ligand also led to stimulation of Smad2 phosphorylation (FIG. 1A). Tryptic phosphopeptide maps of Smad2 phosphorylated in vivo in these cells revealed a nearly identical pattern as compared to phosphorylated Smad2 from MvlLu cells (FIGS. 1E, F, G). Phosphoamino acid analysis of spots 1 through 18, revealed that all were phosphorylated on serine resides except for spot 11 and 18 that contained both phosphoserine and phosphothreonine residues (data not shown). None of the spots contained phosphotyrosine.

Figure 1F:
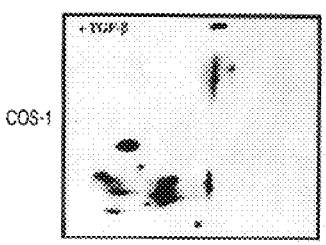
Figure 1G:
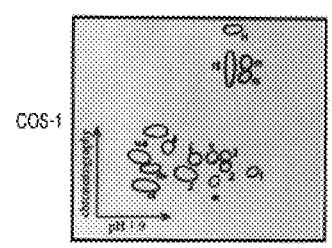
Figure 2A:
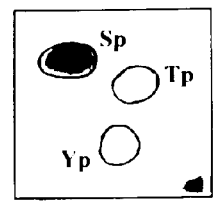
FIGS. 2A–2D show the identification of Ser465 and Ser467 as the major in vivo phosphorylation sites in Smad2.
Figure 2B:
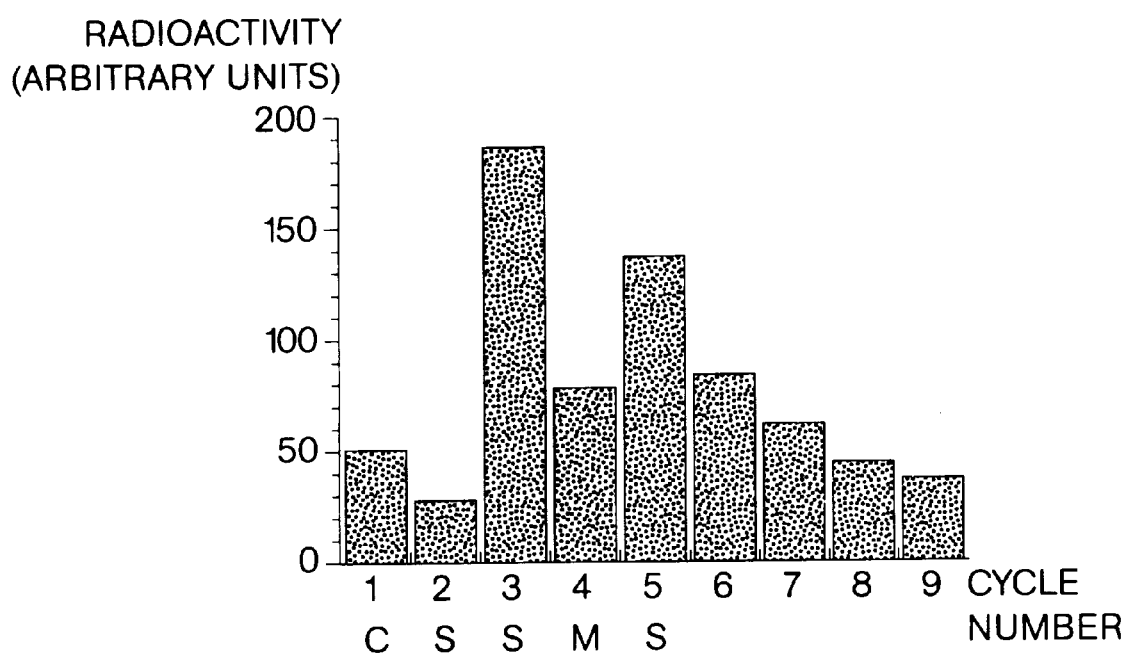
Figure 2C:
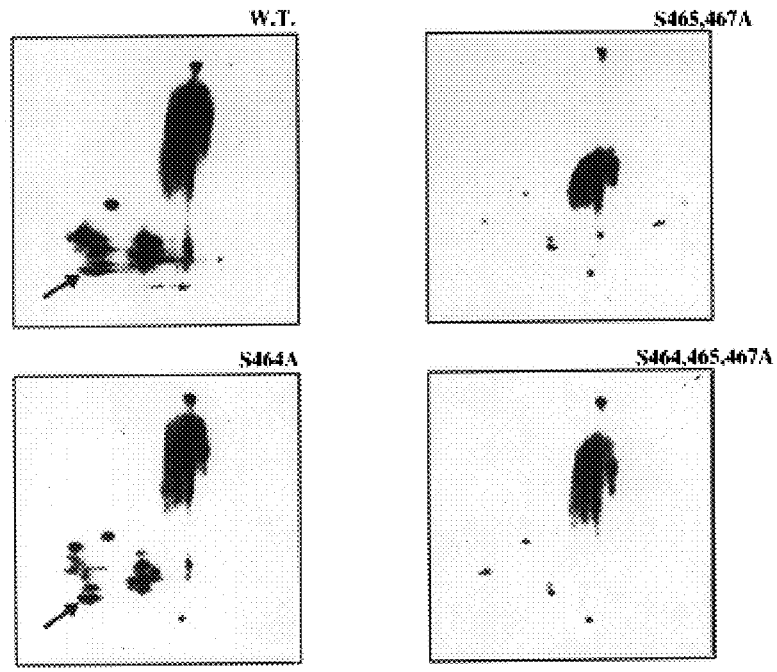

The phosphopeptide corresponding to spot 15 in FIG. 1F was subjected to phosphoamino acid analysis. The migration of phosphorylated serine (Sp), threonine (Tp) and tyrosine (Yp), used as standards, is shown. To identify the positions of phosphorylated residues in the phosphopeptides, the release of radioactivity upon Edman degradation of peptides extracted from the two-dimensional chromatography plate was determined. The elution positions of $^{32}$P-labeled amino acids are shown and aligned to the sequence of the single possible Smad2-derived tryptic peptide containing serine residues in the third and fifth position. The peptide corresponding to spot 15, which contained only phosphoserine, yielded $^{32}$P-radioactivity release in the third and fifth cycles, with some trailing in the following cycles which is characteristic for this method. This indicates that Ser465 and Ser467 in the C-terminus of Smad2 were phosphorylated, since the corresponding tryptic peptide is the only one in the Smad2 with serine residues in position three and five FIGS. 2A, B). The carboxy-terminal tryptic peptide also contained another phosphorylatable amino acid, i.e., Ser464. However, radiochemical sequencing and phosphoamino acid analysis did not reveal phosphoserine at position two in phosphopeptides with the migration position expected if Ser464 would have been phosphorylated alone or in combinations with Ser465 and Ser467. Thus, Ser464 in Smad2 appears not to be phosphorylated in response to TGF-β-stimulation.

In order to confirm that Ser465 and Ser467 are phosphorylation sites in Smad2, these residues and the neighboring Ser464 were mutated to alanine residues singly and in combinations. Wild-type Smad2 (W.T.), as well as Smad2/S464A (S464A), Smad2/S465,467A (S465,467A) and Smad2/S464,465,467A (S464,465,467A) mutants were subjected to two-dimensional phosphopeptide mapping. COS-1 cells were transiently transfected with Smad2 or Smad2 mutants together with TβR-I and TβR-II, and were labeled with [$^{32}$P]orthophosphate. After treatment with TGF-β, wild-type Smad2 or Smad2 mutants were immunoprecipitated and subjected to two-dimensional tryptic phosphopeptide mapping. Sample application points are shown by black squares. The arrows show the migration position of the Ser465 and Ser467 containing tryptic peptide. Analysis of two-dimensional tryptic phosphopeptide maps of wild-type and mutant Smad2 from $^{32}$P-labeled TGF-β-stimulated COS-1 cells, revealed that spot 15, corresponding to a peptide with Ser465 and Ser467 phosphorylated, was not seen in the phosphopeptide map of the Smad2/S465A mutant contained spot 15; the map of the Smad2S454A mutant was in fact identical to that of wild-type Smad2. Moreover, the phosphopeptide map of the triple Smad2/S464, 465, 467A mutant also lacked spot 15, and was identical to that of the Smad2/S465, 467A mutant. Thus, Ser465 and Ser467 are in vivo phosphorylation sites in Smad2.

Figure 2D:
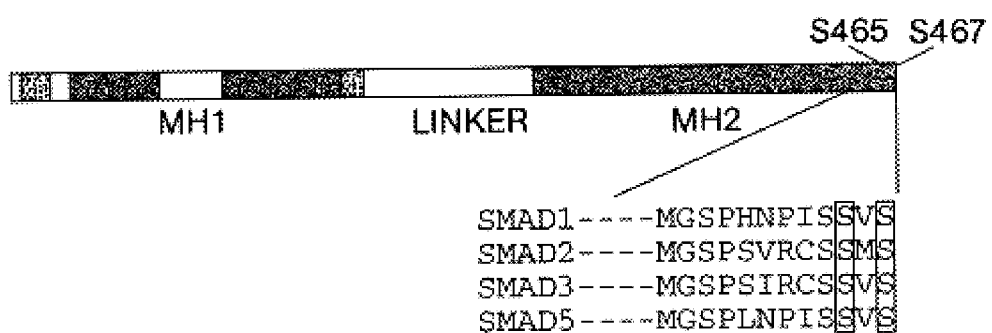

FIG. 2D shows a schematic illustration of Smad2 and C-terminal sequences of Smad1, Smad2, Smad3 and Smad5. Conserved residues are boxed. The C-terminal motif SS(M/V)S (SEQ ID NO: 5) is found in Smad1, Smad2, Smad3, Smad5 and Smad9, and therefore, it is possible that all these Smads are direct substrates for their appropriate activated receptors. In accordance with this possibility a phosphopeptide map of Smad3 from TGF-β-stimulated cells revealed phosphopeptides with similar migration as spot 15 of Smad2; no such spot was found in a map of Smad4, which lacks the C-terminal SS(M/V)S motif.

Example 2

Phosphorylation of Ser465 requires that Ser467 is phosphorylated

Figure 3A:
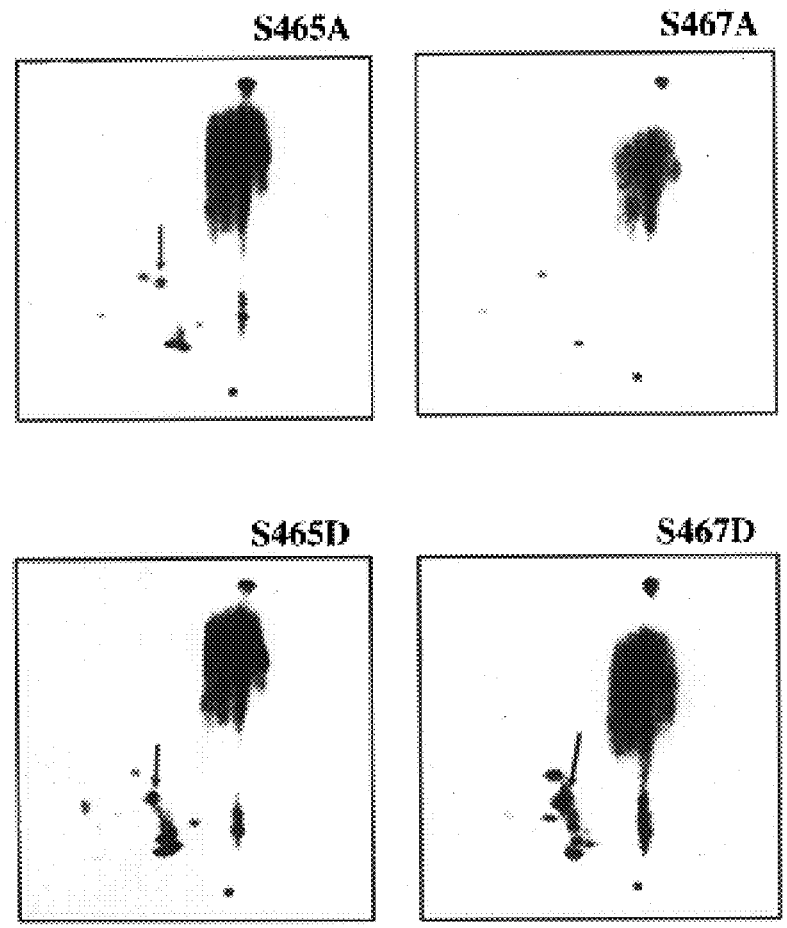
FIGS. 3A–3B demonstrate that phosphorylation of Ser465 requires that Ser467 is phosphorylated.
Figure 3B:
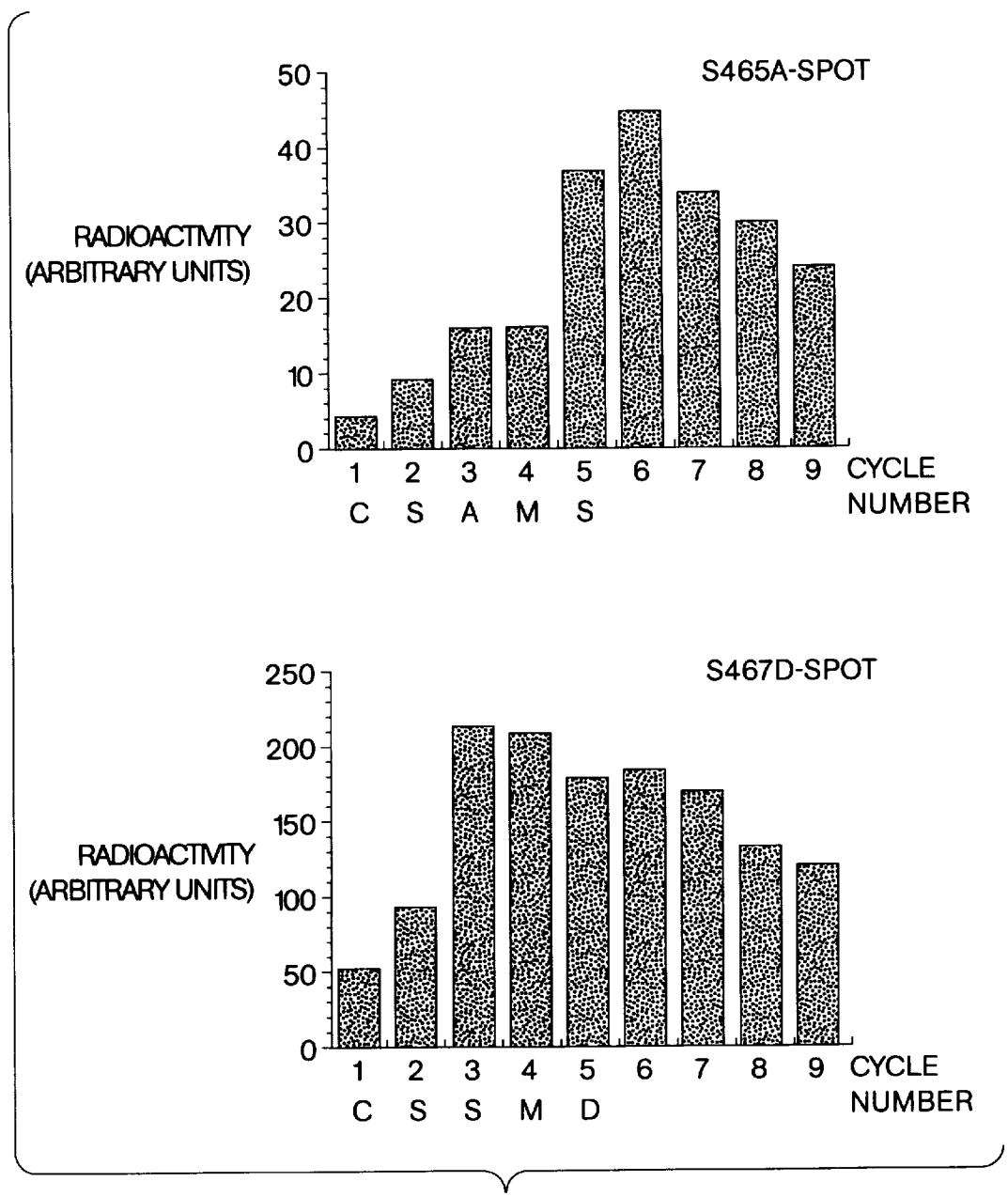

Since Ser465 and Ser467 are located in close proximity of each other, the possibility that they are phosphorylated sequentially was examined. TβR-I-mediated phosphorylation of Smad2 mutants in which Ser465 or Ser467 were converted to alanine or aspartic acid residues was characterized in transfected COS-1 cells. Two-dimensional tryptic phosphopeptide mapping of wild-type Smad2 and Smad2/S465A, Smad2/S465D, Smad2/S467A and Smad2/S467D mutants after co-expression with TGF-β receptors and stimulation with TGF-β, performed as described above, showed loss of spot 15 in all cases. The arrows indicate the migration position of the C-terminal tryptic peptides, which is absent on the map of the Smad2/S467A mutant. Notably, a new spot appeared in the maps of the Smad2/S465A, Smad2/S465D and Smad2/S467D mutants, but not in the map of the Smad2/S467A mutant (FIG. 3A). The new peptide had a shorter migration distance in electrophoresis at pH 1.9 compared to that of spot 15, which is in agreement with a lower degree of phosphorylation of the novel phosphopeptide and suggested that it was phosphorylated at one rather than two residues. Edman degradation elution profiles of the new phosphopeptides appeared on maps of the Smad2/S465A and Smad2/S467D mutants are shown in FIG. 3B. The $^{32}$P-radioactivity released in each cycle was measured. The amino acid sequences of the C-terminals of the Smad2 mutants are presented along with the fraction numbers. When radiochemical sequencing of the novel spot from the map of the Smad2/S465A mutant was performed, radioactivity eluted at the fifth cycle, which is consistent with the expected phosphorylation of the C-terminal tryptic peptide at Ser467 after mutation of Ser465. The fact that the new spot was not seen in the map of the Smad2/S467A mutant suggests that phosphorylation of Ser465 requires phosphorylation of Ser467. The finding that the map of a Smad2/S467D mutant showed the novel spot, suggested that introduction of a negative charge at position 467 could rescue the phosphorylation of Ser465. Radiochemical sequencing of the spot revealed that the peak of radioactivity eluted at the third cycle. This result indicates that Ser465 was phosphorylated in the C-terminal peptide of the Smad2/S467D mutant, and suggests that the requirement for phosphorylation at Ser467 was bypassed by the introduction of a negative charge at this residue.

Example 3

Figure 4:
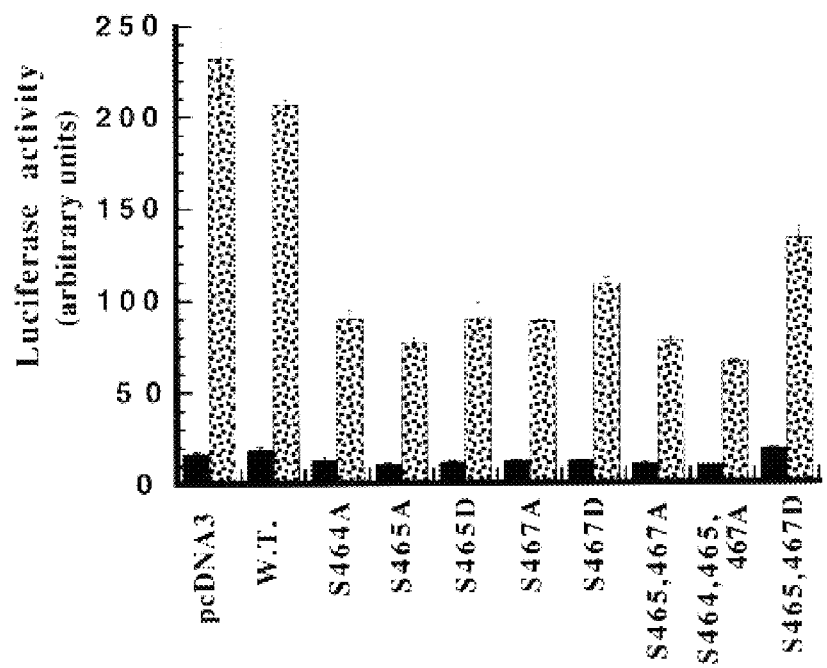
FIG. 4 shows the dominant-negative effect on TGF-β-mediated transcriptional response of Smad2 mutants with serine residues 464, 465 and/or 467 replaced with alanine or aspartic acid residues.

Mutation of Ser464, Ser465 and/or Ser467 in Smad2 interferes with TGF-β-mediated signaling To reveal the importance of Ser464, Ser465 and Ser467 for TGF-β signaling, the ability of Smad2 mutants, in which these residues were replaced with alanine or aspartic acid residues singly or in combinations, to block the TGF-β-mediated transcriptional response was measured using a p3TP-Lux reporter plasmid (FIG. 4). MvlLu cells were transiently transfected with p3TP-Lux plasmid alone or in the presence of Smad2 or Smad2 mutant expression plasmids. Luciferase activity was determined before (■) or after (□) stimulation with 10 ng/ml of TGF-β1. The values were normalized for transfection efficiency using the β-gal reporter gene under transcriptional control of cytomegalovirus promoter. Representative results of three independent experiments are shown. Consistent with previous observations (Zhang et al., 1996), no difference in signaling in the absence or presence of transfected wild-type Smad2 was found, indicating that level of endogenous Smad2 is sufficient for full response. Expression of any Smad2 with Ser465 or Ser467 replaced with alanine residues(s) led to a decrease of the luciferase signal. Introduction of aspartic acid residues, in order to mimic the negative charge of the phosphate group, did not rescue the stimulation of luciferase expression. Notably, Smad2/Ser464A also acted as a dominant negative inhibitor. However, in some experiments, the inhibitory effect of this mutant on TGF-β signaling was less pronounced than those of Smad2/S465A and Smad2/S467A mutants. Thus, Ser464 and in particular the phosphorylatable residues Ser465 and Ser467 in Smad2, are required for TGF-β-induced p3TP-Lux transcriptional response.

Example 4

Association of wild-type Smad2 and Smad2 mutants with TβR-I

Figure 5:
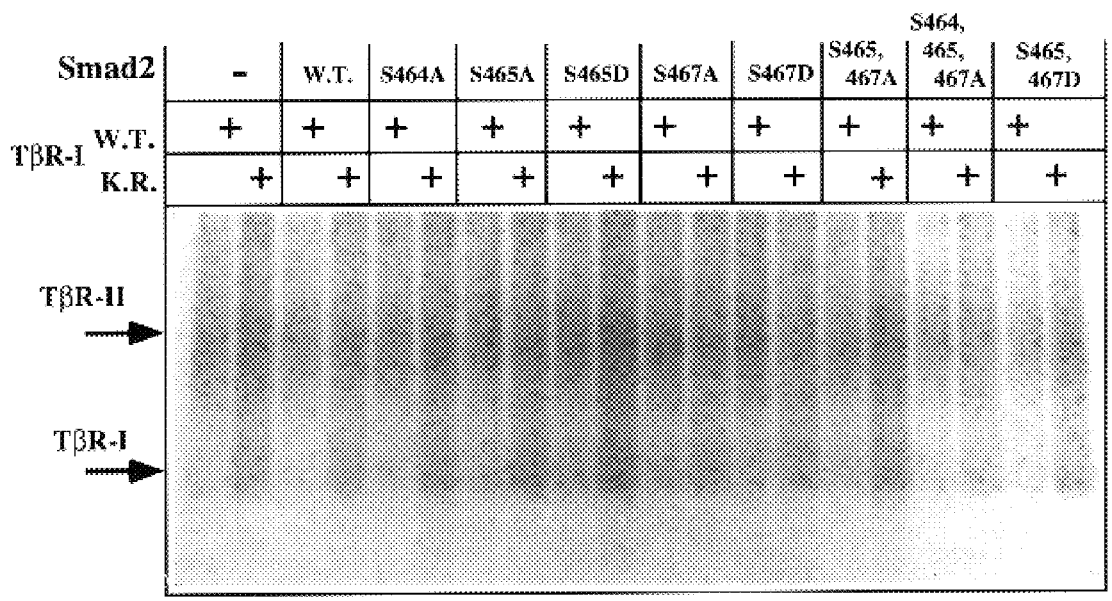
FIG. 5 demonstrates the association of wild-type and mutant Smad2 with TβR-I.

The interaction of Smad2 with the TGF-β receptor complex was investigated by co-expression of wild-type Smad2 and Smad2 mutants with TGF-β receptor sin COS-1 cells (FIG. 5). COS-1 cells were transfected with wild-type Smad2 (W.T.) or Smad2 mutants in combination with TβR-II and wild-type (W.T.) or kinase-inactive (K.R.) forms of TβR-I. Constructs for WT and KR TβR-I tagged at C-terminus with HA epitope were used. The receptors were affinity cross-linked with $^{125}$I-TGF-β1. Cell lysates were subjected to immunoprecipitation with Smad2 antiserum and analyzed by SDS-PAGE and autoradiography. Migration position of TβR-I and TβR-II are shown. Smad2-receptor interaction was determined by the ability of an antiserum against Smad2 to co-immunoprecipitate the receptors, cross-linked with $^{25}$I-TGF-β I. In accordance with previous results (Macías-Silva et al., 1996), it was determined that wild-type Smad2 interacted with TβR-I, provided that TβR-I was kinase-inactive and phosphorylated by TβR-II kinase; in contrast, a Smad2 mutant with the three C-terminal serines altered to alanines, was able to bind with high affinity also to activated wild-type TβR-I. The single and double serine mutants of Smad2 were analyzed in a similar experimental setup for their abilities to interact with wild-type TβR-I or a kinase-inactive TβR-I mutant in complex with TβR-II. The double mutant interacted with TβR-I in a similar manner as the triple mutant. In addition, the single mutants were also found to interact with wild-type TβR-I. Interestingly, although Ser464 is not an in vivo phosphorylation site, Smad2/S464A interacted with TβR-I as efficiently as the Smad2/S465A and Smad2/S467A mutants (FIG. 5). TβR-I and TβR-II were expressed at equal levels, as confirmed by immunoprecipitation of the crosslinked $^{125}$I-TGF-β-receptor complex, followed by SDS-PAGE and autoradiography; also Smad2 was expressed at equal levels as determined by immunoblotting of cell lysates, resolved by SDS-PAGE, with Smad2 antiserum (data not shown). These data are in concordance with the dominant negative effects of Smad2 and mutated at Ser464, Ser465 and/or Ser467 on TGF-β-mediated stimulation of gene expression (FIG. 4), and suggests that the mechanism involves competition of the Smad2 mutants and endogenous Smad2 for binding to TβR-I.

Example 5

Figure 6:
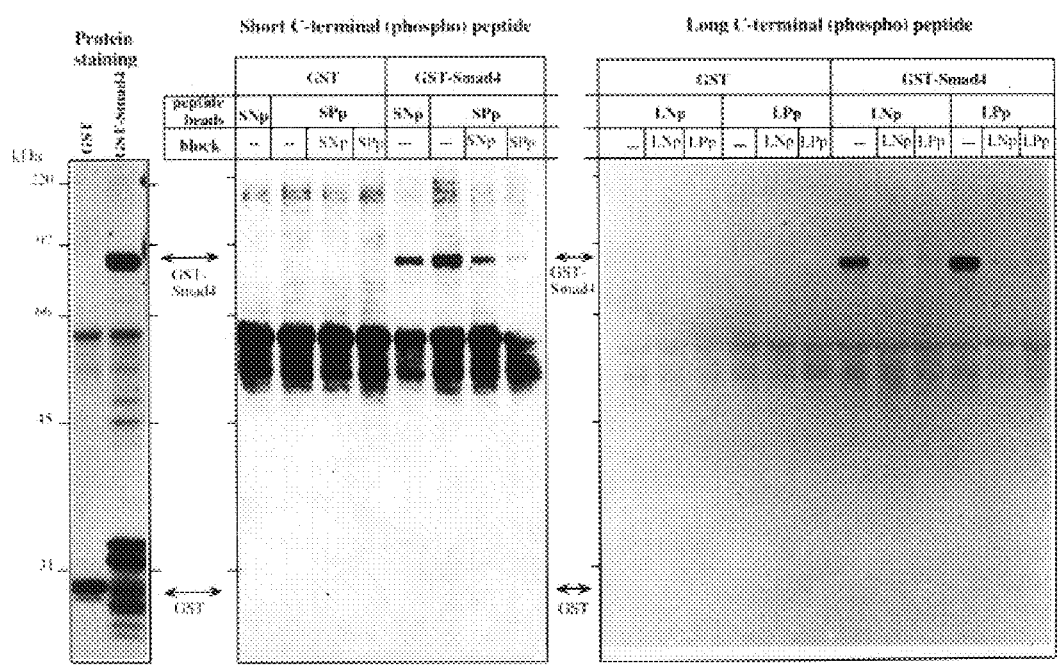
FIG. 6 shows that phosphorylated peptides derived from the C-terminus of Smad2 bind to Smad4.

GST-Smad4 binds with higher affinity to phosphorylated peptides derived from the C-terminus of Smad2 than to the corresponding non-phosphorylated peptides To investigate whether phosphorylated Ser465 and Ser467 of Smad2 are directly involved in heteromeric interaction with Smad4, phosphorylated and non-phosphorylated peptides corresponding to the C-terminus of Smad2 were made and tested for their ability to bind GST-Smad4 fusion proteins. Short C-terminal peptide of Smad2 SSMS (SNp; SEQ ID NO: 3) or its phosphorylated counterpart (SPp), as well as long C-terminal-peptide TQMGSPSVRCSSMS (LNp; SEQ ID NO: 4) or its phosphorylated counterpart (LPp), coupled to CNBr-Sepharose (peptide beads), were incubated with GST or GST-Smad4 fusion protein. For competition large excesses (200 μM) of non-phosphorylated short (SNp) or long (LNp) peptides or their phosphorylated counterpart (SPp and LPp, respectively) were used (block). Proteins bound to the beads, were resolved by SDS-PAGE, transferred to nitrocellulose membrane and immunoblotted with anti-GST antibodies. Migration positions of GST and GST-Smad4 are shown by double arrows. Molecular masses of standard proteins are indicated on the left side on gel in which protein-stained GST and GST-Smad4 are shown. It was found that Smad4 bound to a doubly phosphorylated peptide containing the four C-terminal amino acid residues of Smad2 (SSpMSp SEQ ID: 3), but weakly (or not) to the corresponding non-phosphorylated counterpart (SSMS) (FIG. 6). We also found that the phosphorylated form of a longer peptide containing the 14 C-terminal amino acid residues of Smad2 (TQMGSPSVRCSSpMSp SEQ ID NO: 4) bound GST-Smad4 even more efficiently than the SSpMSp peptide. The phosphorylated long peptide also bound GST-Smad4 more efficiently, than the non-phosphorylated counterpart, however, a considerable binding was observed also to the long non-phosphorylated peptide. This indicates that interaction between Smad2 and Smad4 is not only dependent on phosphorylation of Ser465 and Ser467 in Smad2, but involves also interaction with the sequence upstream of the phosphorylation sites. The interaction was shown to be specific, since it was blocked by an excess of short or long phosphorylated peptides, but not by an excess of an irrelevant phosphopeptide, phosphoserine, or peptides derived from Smad2; the GST protein showed no binding to phosphorylated peptides (FIG. 6; and data not shown).

Example 6

Preparation of Smad2 phospho tail antibody.

Rabbit antisera to TGF-β-receptor-mediated phosphorylated Smad2 was made against the phosphorylated tail of Smad2. A three lysine peptide (KKK) was added to the N-terminus of the amino acids of SEQ ID NO:3 to facilitate coupling to carrier protein. The resulting peptide, KKKSSMS (SEQ ID NO:6), in which underlined serines (amino acids 5 and 7, equivalent to Ser465 and Ser467 of Smad2) are phosphoserines, was coupled to keyhole limpet hemocyanin with glutaraldehyde, mixed with Freund's adjuvant, and used to immunize rabbits according to standard protocols for preparation of polyclonal antibodies. Blood was drawn from immunized rabbits and antisera prepared according to standard procedures. Characterization of the phosphoserine specific antisera (referred to as Smad2 phospho tail antibody) is described in the following examples. Additional Smad2 phosphoserine specific antisera are prepared as described above, using longer Smad2 peptides such as a 14mer peptide (SEQ ID NO:4), 8mer peptides corresponding to amino acids 4–11, 5–12, 6–13 and 7–14 of SEQ ID NO:4, 4mer peptides corresponding to amino acids 8–11, 9–12, and 10–13 of SEQ ID NO:4. Other peptides can be chosen as desired to prepare still other Smad2 phosphoserine specific antisera. One or more of the serine residues in the foregoing peptides are phosphorylated.

Example 7

Smad2 phospho tail antibody recognizes TGF-β type I receptor mediated phosphorylated Smad2 by Western blot analysis.

Figure 7:
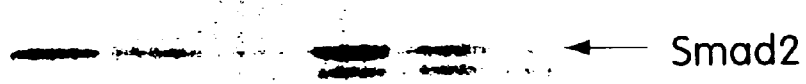
FIG. 7 demonstrates the specificity of a Smad2 phospho tail antibody for phosphorylated Smad2.

COS cells were transfected with TGF-β type I and type II receptors and Smad2 expression plasmids in the absence or presence of different amounts of Smad7 expression plasmid. Cells were treated without or with TGF-β, and cell lysates were prepared and used for Western blotting using the Smad2 phospho tail antibody prepared in Example 6. The results of these experiments are shown in FIG. 7. In the absence of Smad7 and TGF-β, Smad2 is weakly phosphorylated (lane 1), which is increased after ligand addition (lane 4). The phosphorylation in the absence of ligand is caused by ligand independent heteromeric complex formation of receptors in COS cells. In the presence of increasing amounts of Smad7, which inhibits receptor dependent Smad2 phosphorylation on Ser465 and Ser467 in C-tail, a dose dependent decrease in Smad2 phosphorylation was observed. Thus the Smad2 phospho tail antibody recognized TGF-β type I receptor mediated phosphorylated Smad2. The same blot was reprobed with Smad2 specific antibody; the equal expression of Smad2 in each transfection was shown.

Example 8

Smad2 phospho tail antibody recognizes phosphorylated Smad2 in extracts from metabolically labeled and TGF-β stimulated cells.

Figure 8:
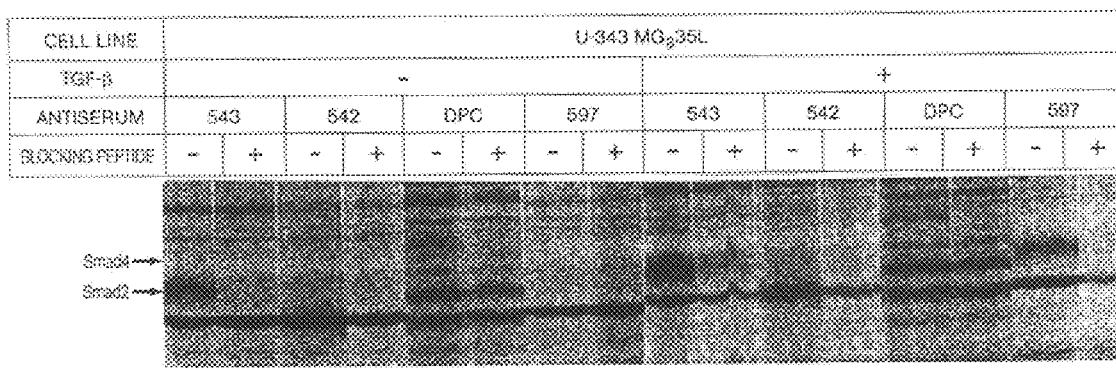
FIG. 8 shows that the Smad2 phospho tail antibody recognizes Smad2 phosphorylated in TGF-β stimulated cells.

To determine whether the Smad2 phospho tail antibody binds Smad2 phosphorylated following TGF-β stimulation, the glioblastoma cell line U-343 MGa 35 L was metabolically labeled with $^{35}$S-methionine and $^{35}$S-cysteine for 4 hours. During the last hour of labeling cells were incubated with or without 10 ng/ml TGF-β1. Cell lysates were precleaned by incubation with protein A-Sepharose beads. After centrifugation to remove the protein A-Sepharose beads, the cell extracts were subjected to immunoprecipitation using Smad-specific antisera. Antiserum '543' recognizes Smad2, '542' is specific for Smad3, 'DPC' is raised towards Smad 4 and '597' is the Smad2 phospho tail antibody prepared in Example 6. To show specificity of the antisera, controls were included containing the respective peptides to which the antisera were raised. Incubations were done for 2 hours after which the immunocomplexes were collected on protein-A Sepharose beads. The beads were washed three times with lysis buffer (125 mM NaCl, 10 mM Tris-HCl pH 7.5, 1 mM EDTA, 1 mM PMSF, 1.5% trasylol, and 1% Triton X-100), three times with RIPA buffer (150 mM NaCl, 0.1% SDS, 0.5% deoxycholate, 0.5% Triton X-100, 50 mM Tris-HCl pH 8.0), and three times with high salt buffer (20 mM Tris-HCl pH 7.5, 500 mM NaCl, 1% Triton X-100). Immunocomplexes were separated on a 8.5% SDS-PAGE gel and visualized using a Fuji-X BioImager. As shown in FIG. 8, U-343 MGa 35L clearly expressed Smad2 protein as specifically recognized by the 543 antiserum (lanes 1, 2, 9 and 10), while Smad4 was brought down by the DPC antibody (lanes 5, 6, 13, 14). Smad3 protein was not detected in these cells. In the absence of TGF-β1, the Smad2 phospho tail antiserum (597) did not detect any Smad protein (lanes 7, 8). Upon treatment of the cells for one hour with 10 ng/ml of TGF-β1, Smad2 phospho tail antibody clearly and specifically recognized phosphorylated Smad2 (lanes 11, 12). These data indicate that the Smad2 phospho tail antiserum can be successfully applied for the detection of TGF-β induced phosphorylated Smad2 present in extracts from metabolically labeled cells.

Example 9

Preparation of phospho tail antibodies which recognize pathway restricted Smad1, Smad3, Smad5, and Smad9.

Rabbit antisera to TGF-β-receptor-mediated phosphorylated Smad1, Smad3, Smad5, and Smad9 are made against peptides representing the phosphorylated tail of these Smad proteins. A three lysine peptide (KKK) is added to the N-terminus of the amino acids of SEQ ID NO:8 (SSVS) to facilitate coupling to carrier protein. The resulting peptides, e.g. KKKSSVS (SEQ ID NO:9), in which one or more of the serines are phosphoserines is coupled to keyhole limpet hemocyanin with glutaraldehyde. Longer peptides are used as needed to prepare Smad-specific antibodies. For example, additional peptides are prepared by the addition of the KKK linker to longer peptides derived from the C-terminus of Smad1, Smad3, Smad5 and Smad9, e.g. 14mers analogous to SEQ ID NO:4 including SEQ ID NO:10, SEQ ID NO:11, SEQ ID NO:12, and SEQ ID NO:13, or intermediate length peptides such as 8mers corresponding to amino acids 7–14 of SEQ ID NO:10, SEQ ID NO:11, SEQ ID NO:12, and SEQ ID NO:13. Still other peptides are used to prepare antibodies to pathway-restricted Smad proteins, including Smad C-terminal peptides which lack the two most C-terminal amino acids (e.g., 4mers corresponding to amino acids 9–12 of SEQ ID NO:10, SEQ ID NO:11, SEQ ID NO:12, and SEQ ID NO:13, or 8mers corresponding to amino acids 5–12 of SEQ ID NO:10, SEQ ID NO:11 SEQ ID NO:12, and SEQ ID NO:13). For all of the foregoing peptides, one or more of the C-terminal serine residues are phosphorylated.

The coupled peptides are mixed with Freund's adjuvant and is used to immunize rabbits according to standard methods for preparing polyclonal antibodies. Blood is drawn from immunized rabbits and antisera prepared according to standard procedures. Characterization of the phosphoserine specific antisera is described in the following examples. The specificity of the polyclonal antibodies for phosphorylated pathway-restricted Smad proteins and not nonphosphorylated pathway-restricted Smad proteins can be tested by methods well known to one of ordinary skill in the art, including immunoprecipitation and Western blotting. Antisera to phosphorylated pathway-restricted Smad proteins which crossreact with nonphosphorylated pathway-restricted Smad proteins can be affinity purified, if desired, to obtain polyclonal antibodies which recognize only phosphorylated pathway-restricted Smad proteins. Alternatively, monoclonal antibodies to phosphorylated pathway-restricted Smad proteins can be prepared as described below in Example 12. Each hybridoma clone producing monoclonal antibodies can be tested for expression of antibodies which recognize selectively the phosphorylated form of pathway-restricted Smad proteins according to standard methods.

Example 10

Pathway-restricted Smad phospho tail antibodies recognize TGF-β superfamily type I receptor-mediated phosphorylated pathway-restricted Smads by Western blot analysis.

COS cells are transfected as described in Example 7 with TGF-β superfamily type I and type II receptors and a pathway-restricted Smad expression plasmid (Smad1, Smad3, Smad5, or Smad9), in the absence or the presence of different amounts of Smad7 expression plasmid. For testing antibodies which recognize phosphorylated Smad1, Smad5 or Smad9, cells are transfected with BMP type I and type II receptors and a Smad1, Smad5 or Smad9 expression plasmid. For testing antibodies which recognize phosphorylated Smad3, cells are transfected with TGF-β or activin type I and type II receptors and a Smad3 expression plasmid. Cells then are treated with or without TGF-β, activin or BMP molecules according to the receptors transfected, and cell lysates are prepared and are used for Western blotting using pathway specific Smad phospho tail antisera according to standard procedures. In the presence of TGF-β, activin or BMP molecules, the pathway specific Smads are phosphorylated and recognized by the phospho tail antibodies. Antibodies which are selective for individual phosphorylated Smad proteins can be identified by blocking experiments using the various peptides against which the antibodies are raised (and non-phosphorylated peptides). For example, an antibody raised against a Smad1 phosphopeptide which does not bind the cognate antigen in the presence of excess Smad1 phosphopeptide, but does bind the cognate antigen in the presence of nonphosphorylated Smad1 peptide or Smad3, Smad5 and/or Smad9 phosphopeptides is an antibody which selectively binds Smad1 phosphorylated at the C-terminus. Therefore the pathway restricted Smad phospho tail antibodies recognize TGF-β type I receptor-mediated phosphorylated pathway specific Smads.

Example 11

Pathway specific Smad phospho tail antibody recognizes phosphorylated pathway specific Smads in extracts from metabolically labeled and TGF-β stimulated cells.

Cells lines which overexpress pathway restricted Smads (e.g., naturally overexpress, or which are transfected with expression plasmids) are metabolically labeled with $^{35}$S-methionine and $^{35}$S-cysteine for 4 hours. During the last hour of labeling, cells are incubated with or without 10 ng/ml TGF-β1. Cells are lysed according to standard procedures. Cell lysates are precleaned by incubation with protein A-Sepharose beads. After centrifugation to remove the beads, the cell extracts are subjected to immunoprecipitation using the pathway specific Smad phospho tail antisera. To show specificity of the antisera, controls are included containing the respective pathway specific Smad peptides to which the antisera have been raised. Incubations are done for 2 hours, after which the immunocomplexes are collected on protein-A Sepharose beads. The beads are washed three times with lysis buffer (125 mM NaCl, 10 mM Tris-HCl pH 7.5, 1 mM EDTA, 1 mM PMSF, 1.5% trasylol, and 1% Triton X-100), three times with RIPA buffer (150 mM NaCl, 0.1% SDS, 0.5% deoxycholate, 0.5% Triton X-100, 50 mM Tris-HCl pH 8.0), and three times with high salt buffer (20 mM Tris-HCl pH 7.5, 500 mM NaCl, 1% Triton X-100). Immunocomplexes are separated on a 8.5% SDS-PAGE gel and visualized using a Fuji-X BioImager. Upon treatment of the cells for one hour with 10 ng/ml of TGF-β1, pathway specific Smad phospho tail antibodies clearly and specifically recognize phosphorylated pathway specific Smad proteins. Therefore the antibodies effectively immunoprecipitate the respective pathway specific Smad proteins present in extracts from metabolically labeled cells.

Example 12
Preparation of monoclonal antibodies

1. Immunization of mice

Mice (e.g., Balb/c female; Jackson Laboratories, Bar Harbor, Me.) are immunized by subcutaneous and/or intraperitoneal injection with a pathway-restricted Smad peptide having one or more C-terminal phosphorylated serine residues suspended in Dulbecco's phosphate buffered saline, then emulsified with an equal volume of complete Freund's adjuvant (Sigma Chemical Co., St. Louis, Mo.). The mice are given two intraperitoneal booster immunizations of phosphorylated Smad peptide suspended in Dulbecco's phosphate buffered saline (GIBCO, Grand Island, N.Y.), then emulsified with an equal volume of incomplete Freund's adjuvant (Sigma Chemical Co., St. Louis, Mo.) at 14 day intervals following the initial immunization.

2. Screening of mice for antibody production

The presence of antibodies to phosphorylated Smad peptide is tested by immunoprecipitation or Western blotting according to standard procedures. For example, ten days following the third and final immunization, a small amount of blood is collected by retro-orbital bleed from each mouse and is clotted. A 1:1000 dilution of each of the serum samples collected from the immunized mice (50 $\mu$l) is added to a sample of labeled phosphorylated Smad peptide (labeling can be, e.g., $^{32}$P phosphorylation, biotin conjugation, inclusion of a Flag antibody tag, etc.), mixed well and incubated for 60 minutes at 4° C. Protein A-Sepharose is added to the reaction and incubated for 30 min at 4° C. The bound antibody is recovered by centrifugation. Pellets are washed, and SDS-PAGE sample buffer added followed by boiling to disrupt immune complexes. The samples are then analyzed by SDS-PAGE and autoradiography (for radioactive labeling) or other detection method such as chemiluminescence. Alternatively, radioactivity in the washed pellets is measured by scintillation counting. The mouse sera exhibiting the highest degree of binding to phosphorylated Smad peptide is selected for cell fusion to create the monoclonal antibodies.

3. Preparation of hybridomas

Hybridoma cell lines are prepared according to standard protocols; one example is provided below. Briefly, after the mouse with the best antibody titre to the phosphorylated Smad peptide is selected, it is rested for a total of 4 weeks after its last immunization. The mouse is then boosted with phosphorylated Smad peptide by intraperitoneal injection in Dulbecco's phosphate buffered saline. Four days later, the mouse is euthanized by cervical dislocation and the spleen is removed and teased apart into a cell suspension and washed in Dulbecco's phosphate buffered saline. The spleen cells are counted and mixed with SP 2/0 myeloma cells (ATCC Accession No. CRL8006, Rockville, Md.) that are incapable of secreting either heavy or light immunoglobulin chains (Kearney et al., *J. Immunology*, 123:1548, 1979) at a ratio of 2:1 (spleen cell:myeloma cells) and then fused using polyethylene glycol 1450 (ATCC, Rockville, Md.) according to the standard procedure developed by Kohler and Milstein (*Nature,* 256:495, 1975) in eight 96-well tissue culture plates in selective HAT medium.

Between 10 and 21 days after fusion, hybridoma colonies become visible and are screened by immunprecipitation, as described above. Alternatively, ELISA assays or other immunobinding assay can be used to determine which hybridomas produce antibodies that bind phosphorylated Smad peptide. All hybridoma colonies that give a positive response are expanded to 24-well cultures and subcloned by limiting dilution to produce monoclonal cell lines. At this point, additional screening is done with the hybridomas to identify which hybridoma produces an anti-Smad protein antibody. Culture media harvested from hybridoma cultures (supernatants) are screened as described above, e.g. by ELISA (enzyme-linked immuno-adsorbent assay) to identify positive clones.

The monoclonal antibodies optionally are examined to determine the subclass of the antibody using an typing kit such as an ISOstrip Kit (Boehringer Mannheim, Indianapolis, Ind.). A small aliquot (e.g., 5 $\mu$l) of hybridoma supernatant is diluted in PBS and added to a test tube containing blue latex beads bound to anti-mouse Ig antibodies. An isotyping strip is then placed in each tube and the bead/antibody solution moves up the strip by capillary action until the solution passes an antibody bound line containing antibodies specific for the different isotypes. A blue line appears in the area of the strip for each isotype detected in the hybridoma supernatant.

Example 13
Separation and sequencing of the heavy and light chains of anti-Smad monoclonal antibody The antibody may be isolated from the hybridomas and purified by any method known in the art. At least two methods may be used to separate the heavy and light chains of the purified antibody for sequence determination. The first method employs a semi-preparative SDS-PAGE followed by electroblotting onto a polyvinyldifluoride (PVDF) membrane. Briefly, the purified antibody is subjected to slab gel electrophoresis in SDS after reduction with 2-merecaptoethanol. The resolved heavy and light chains are then transferred onto a membrane such as an IMMOBILON® membrane (a PVDF membrane from Millipore, Bedford, Mass.) using the electroblotting method of Matsudaira (*J. Biol. Chem.* 261:10035, 1987). Bands corresponding to the heavy and light chains which are identified with Coomassie Brilliant Blue staining may then be excised from the membrane and processed for N-terminal sequencing.

A second more complicated method permits larger amounts of the heavy and light chains to be isolated in solution. This method involves a dialysis step in which the purified antibody sample is dialyzed against 0.1M Tris-HCl, 1 mM EDTA, pH 8.0, at 4° C. and then subjected to oxidative sulfitolysis in $NaSO_3Na_2S_2O_0$, essentially as described by Morehead at al. (*Biochemistry* 23:2500, 1984). Following sulfitolysis, the antibody preparation is dialyzed against 1M acetic acid, lyophilized to dryness, reconstituted in 1M acetic acid, and subjected to gel filtration in a SEPHADEX G-75 column in 1M acetic acid. The purity of the heavy and light chains following this step can then be assessed by analytical SDS-PAGE and then concentrated for sequencing.

N-terminal amino acid sequencing may be performed using any commercial amino acid sequencer such as an Applied Biosystems Model 477A protein-peptide sequencer. Analysis of the isolated chains is performed following the instructions of the manufacturer of the sequencer.

Example 14
Oligonucleotide primer design and cloning of Smad phospho tail monoclonal antibody nucleic acids 1. Preparation of Oligonucleotides Based upon the information which is obtained from the foregoing amino acid sequence analyses, degenerate oligonucleotide primers can be designed for use in PCR. Other non-degenerate primers may be designed based upon nucleotide sequence information obtained following PCR amplification of cDNA encoding the complete heavy and light chains.

Oligonucleotide primers are synthesized by standard methods using a commercially available sequencer such as an Applied Biosystems Model 380B Synthesizer.

Alternatively, PCR amplification of the IgG, Fd heavy chain fragments and light chains may be performed using the individual heavy and light chain variable region gene families, and 3' constant region primers for $IgG_1$, k or l as previously described (Kang et al., in *Methods, A Companion to Methods in Enzymology:* Vol. 2, R. A. Lerner and D. R. Burton, ed. Academic Press, NY, pp 111–118, 1991). Primers may contain restriction enzyme sites to allow the sequential ligation of Fd and light chain libraries for various other recombinant uses into a phage display vector.

2. PCR Amplification and DNA Sequencing of Heavy and Light Chains

Total cytoplasmic RNA is isolated from the hybridoma cell lines by any method known in the art. First strand cDNA is synthesized directly from total cytoplasmic RNA using reverse transcriptase. Polymerase chain reaction (PCR) amplifications then are carried out according to standard protocols using a thermal cycler or similar equipment. After amplification aliquots of the PCR mixtures are subjected to electrophoresis in agarose gels containing ethidium bromide. The PCR fragments of interest are excised from the gels and purified by e.g. electroelution. The gel-purified PCR fragments are digested with appropriate restriction enzymes and ligated to a cloning vector such as pBluescript. Competent bacterial cells are transformed with the ligation mixture, grown, and lysed for preparation of DNA. Plasmid DNA is purified by any technique known in the art for purifying DNA, such as the Qiagen plasmid maxiprep kit (Qiagen, Chatsworth, Calif.). Sequencing is then performed on an automated DNA sequencer. Derived sequences for heavy chain Fd fragments and light chains can then be aligned using various commercially available software packages and the Genbank database.

Equivalents

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

A sequence listing is presented followed by what is claimed:

---

What is claimed is:

1. An isolated Smad2 polypeptide comprising a polypeptide having the amino acid sequence of SEQ ID NO:2 or its human homolog except that the polypeptide includes a mutation comprising a non-serine amino acid located at one or more of amino acids 464, 465 and 467.

2. The isolated Smad2 polypeptide of claim 1 wherein the mutation is located at positions selected from the group consisting of 464; 465; 467; 464 and 465; 464 and 467; 465 and 467; and 464, 465 and 467.

3. The isolated Smad2 polypeptide of claim 1 wherein the mutation is selected from the group consisting of Ser464Ala; Ser465Ala; Ser467Ala; Ser464Ala and Ser465Ala; Ser464Ala and Ser467Ala; Ser465Ala and Ser467Ala; and Ser464Ala, Ser465Ala and Ser465Ala.

4. The isolated Smad2 polypeptide of claim 3, wherein the mutation is Ser464Ala.

5. The isolated Smad2 polypeptide of claim 3, wherein the mutation is Ser465Ala.

6. The isolated Smad2 polypeptide of claim 3, wherein the mutation is Ser467Ala.

7. The isolated Smad2 polypeptide of claim 3, wherein the mutation is Ser464Ala and Ser465Ala.

8. The isolated Smad2 polypeptide of claim 3, wherein the mutation is Ser464Ala and Ser467Ala.

9. The isolated Smad2 polypeptide of claim 3, wherein the mutation is Ser465Ala and Ser467Ala.

10. The isolated Smad2 polypeptide of claim 3, wherein the mutation is Ser464Ala, Ser465Ala and Ser467Ala.

11. An isolated Smad4 binding polypeptide comprising the amino acid sequence of SEQ ID NO:3, provided that the isolated polypeptide is not SEQ ID NO:2.

12. The isolated Smad4 binding polypeptide of claim 11, wherein the isolated polypeptide is phosphorylated on one or more amino acids selected from the group consisting of the first most C-terminal amino acid of SEQ ID NO:2, the third most C-terminal amino acid of SEQ ID NO:2 and the fourth most C-terminal amino acid of SEQ ID NO:2.

13. The isolated Smad4 binding polypeptide of claim 11, wherein the isolated polypeptide comprises a polypeptide selected from the group consisting of the 4 most C-terminal amino acids of SEQ ID NO:2, the 5 most C-terminal amino acids of SEQ ID NO:2, the 6 most C-terminal amino acids of SEQ ID NO:2, the 7 most C-terminal amino acids of SEQ ID NO:2, the 8 most C-terminal amino acids of SEQ ID NO:2, the 9 most C-terminal amino acids of SEQ ID NO:2, the 10 most C-terminal amino acids of SEQ ID NO:2, the 11 most C-terminal amino acids of SEQ ID NO:2, the 12 most C-terminal amino acids of SEQ ID NO:2, the 13 most C-terminal amino acids of SEQ ID NO:2, the 14 most C-terminal amino acids of SEQ ID NO:2, the 15 most C-terminal amino acids of SEQ ID NO:2, the 16 most C-terminal amino acids of SEQ ID NO:2, the 17 most C-terminal amino acids of SEQ ID NO:2, the 18 most C-terminal amino acids of SEQ ID NO:2, the 19 most C-terminal amino acids of SEQ ID NO:2, and the 20 most C-terminal amino acids of SEQ ID NO:2.

14. The isolated Smad4 binding polypeptide of claim 13, wherein the isolated polypeptide comprises the amino acid sequence of SEQ ID NO:4.

15. The isolated Smad4 binding polypeptide of claim 13, wherein the isolated polypeptide is phosphorylated on one or more amino acids selected from the group consisting of the first most C-terminal amino acid of SEQ ID NO:2, the third most C-terminal amino acid of SEQ ID NO:2 and the fourth most C-terminal amino acid of SEQ ID NO:2.

16. The isolated Smad4 binding polypeptide of claim 14, wherein the isolated polypeptide is phosphorylated on one or more amino acids selected from the group consisting of the first most C-terminal amino acid of SEQ ID NO:2, the third most C-terminal amino acid of SEQ ID NO:2 and the fourth most C-terminal amino acid of SEQ ID NO:2.

* * * * *

UNITED STATES PATENT AND TRADEMARK OFFICE
CERTIFICATE OF CORRECTION

PATENT NO. : 6,103,869
DATED : August 15, 2000
INVENTOR(S): Souchelnytskyi et al.

It is certified that error appears in the above-identified patent and that said Letters Patent is hereby corrected as shown below:

On the first page of the patent under [75] Inventors:

Please replace "Serhiy Souchelnytokyi" with --Serhiy Souchelnytskyi--.

Please replace "Ulla Engetröm" with --Ulla Engström--.

Please replace "Peter ton Dijke" with --Peter ten Dijke--.

Signed and Sealed this

Twenty-fourth Day of April, 2001

Attest:

NICHOLAS P. GODICI

Attesting Officer

Acting Director of the United States Patent and Trademark Office

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
        (A) LENGTH: 1639 base pairs
        (B) TYPE: nucleic acid
        (C) STRANDEDNESS: double
        (D) TOPOLOGY: linear (iii) HYPOTHETICAL: NO (iv) ANTISENSE: NO (ix) FEATURE:

(A) NAME/KEY: Coding Sequence
        (B) LOCATION: 60...1460
        (D) OTHER INFORMATION:

(xi) SEQUENCE DESCRIPTION: SEQ ID NO:1:

```
CCCGGAGGGT AGATTTACCG GGCTTTTTCT GAGTGTGGAT TGTTACCTTT GGTAAGAAA          59

ATG TCG TCC ATC TTG CCA TTC ACT CCG CCA GTG GTG AAG AGA CTT CTG         107
Met Ser Ser Ile Leu Pro Phe Thr Pro Pro Val Val Lys Arg Leu Leu
 1               5                  10                  15

GGA TGG AAA AAA TCA GCC GGT GGG TCT GGA GGA GCA GGT GGT GGA GAG         155
Gly Trp Lys Lys Ser Ala Gly Gly Ser Gly Gly Ala Gly Gly Gly Glu
            20                  25                  30

CAG AAT GGA CAG GAA GAA AAG TGG TGT CAA AAA GCA GTG AAA AGT CTG         203
Gln Asn Gly Gln Glu Glu Lys Trp Cys Gln Lys Ala Val Lys Ser Leu
        35                  40                  45

GTG AAA AAG CTA AAG AAA ACA GGA CGG TTA GAT GAG CTT GAG AAA GCC         251
Val Lys Lys Leu Lys Lys Thr Gly Arg Leu Asp Glu Leu Glu Lys Ala
    50                  55                  60

ATC ACC ACT CAG AAT TGC AAT ACT AAA TGT GTC ACC ATA CCA AGC ACT         299
```

```
Ile Thr Thr Gln Asn Cys Asn Thr Lys Cys Val Thr Ile Pro Ser Thr
65                  70                  75                  80

TGC TCT GAA ATT TGG GGA CTG AGT ACA GCA AAT ACG GTA GAT CAG TGG    347
Cys Ser Glu Ile Trp Gly Leu Ser Thr Ala Asn Thr Val Asp Gln Trp
                85                  90                  95

GAC ACA ACA GGC CTT TAC AGC TTC TCT GAA CAA ACC AGG TCT CTT GAT    395
Asp Thr Thr Gly Leu Tyr Ser Phe Ser Glu Gln Thr Arg Ser Leu Asp
                100                 105                 110

GGC CGT CTT CAG GTT TCA CAC CGG AAA GGG TTG CCA CAT GTT ATA TAT    443
Gly Arg Leu Gln Val Ser His Arg Lys Gly Leu Pro His Val Ile Tyr
        115                 120                 125

TGC CGG CTC TGG CGC TGG CCG GAC CTT CAC AGT CAT CAT GAG CTC AAG    491
Cys Arg Leu Trp Arg Trp Pro Asp Leu His Ser His His Glu Leu Lys
130                 135                 140

GCA ATC GAA AAC TGC GAA TAT GCT TTT AAT CTG AAA AAA GAT GAA GTG    539
Ala Ile Glu Asn Cys Glu Tyr Ala Phe Asn Leu Lys Lys Asp Glu Val
145                 150                 155                 160

TGT GTA AAT CCG TAC CAC TAC CAG AGA GTT GAG ACC CCA GTC TTG CCT    587
Cys Val Asn Pro Tyr His Tyr Gln Arg Val Glu Thr Pro Val Leu Pro
                165                 170                 175

CCA GTC TTA GTG CCT CGG CAC ACG GAG ATT CTA ACA GAA CTG CCG CCC    635
Pro Val Leu Val Pro Arg His Thr Glu Ile Leu Thr Glu Leu Pro Pro
                180                 185                 190

CTG GAT GAC TAC ACC CAC TCC ATT CCA GAA AAC ACA AAT TTC CCA GCA    683
Leu Asp Asp Tyr Thr His Ser Ile Pro Glu Asn Thr Asn Phe Pro Ala
                195                 200                 205

GGA ATT GAG CCA CAG AGT AAT TAC ATC CCA GAA ACA CCA CCA CCT GGA    731
Gly Ile Glu Pro Gln Ser Asn Tyr Ile Pro Glu Thr Pro Pro Pro Gly
210                 215                 220

TAT ATC AGT GAA GAT GGA GAA ACA AGT GAC CAA CAG TTG AAC CAA AGT    779
Tyr Ile Ser Glu Asp Gly Glu Thr Ser Asp Gln Gln Leu Asn Gln Ser
225                 230                 235                 240

ATG GAC ACA GGC TCT CCG GCT GAA CTG TCT CCT ACT ACT CTC TCT CCT    827
Met Asp Thr Gly Ser Pro Ala Glu Leu Ser Pro Thr Thr Leu Ser Pro
                245                 250                 255

GTT AAT CAC AGC TTG GAT TTG CAG CCA GTT ACT TAC TCG GAA CCT GCA    875
Val Asn His Ser Leu Asp Leu Gln Pro Val Thr Tyr Ser Glu Pro Ala
                260                 265                 270

TTC TGG TGT TCA ATC GCA TAC TAT GAA CTA AAC CAG AGG GTT GGA GAG    923
Phe Trp Cys Ser Ile Ala Tyr Tyr Glu Leu Asn Gln Arg Val Gly Glu
                275                 280                 285

ACC TTC CAT GCG TCA CAG CCC TCG CTC ACT GTA GAC GGC TTC ACA GAC    971
Thr Phe His Ala Ser Gln Pro Ser Leu Thr Val Asp Gly Phe Thr Asp
        290                 295                 300

CCA TCA AAC TCG GAG AGG TTC TGC TTA GGC TTG CTC TCC AAC GTT AAC    1019
Pro Ser Asn Ser Glu Arg Phe Cys Leu Gly Leu Leu Ser Asn Val Asn
305                 310                 315                 320

CGA AAT GCC ACT GTA GAA ATG ACA AGA AGA CAT ATA GGA AGG GGA GTG    1067
Arg Asn Ala Thr Val Glu Met Thr Arg Arg His Ile Gly Arg Gly Val
                325                 330                 335
```

```
CGC TTG TAT TAC ATA GGT GGG GAA GTG TTT GCT GAG TGC CTA AGT GAT    1115
Arg Leu Tyr Tyr Ile Gly Gly Glu Val Phe Ala Glu Cys Leu Ser Asp
        340                 345                 350

AGT GCA ATC TTT GTG CAG AGC CCC AAC TGT AAC CAG AGA TAC GGC TGG    1163
Ser Ala Ile Phe Val Gln Ser Pro Asn Cys Asn Gln Arg Tyr Gly Trp
            355                 360                 365

CAC CCT GCA ACA GTG TGT AAG ATC CCA CCA GGC TGT AAC CTG AAG ATC    1211
His Pro Ala Thr Val Cys Lys Ile Pro Pro Gly Cys Asn Leu Lys Ile
        370                 375                 380

TTC AAC AAC CAA GAA TTT GCT GCT CTT CTG GCT CAG TCT GTC AAC CAG    1259
Phe Asn Asn Gln Glu Phe Ala Ala Leu Leu Ala Gln Ser Val Asn Gln
385                 390                 395                 400

GGT TTT GAA GCC GTT TAT CAG CTA ACC CGA ATG TGC ACC ATA AGA ATG    1307
Gly Phe Glu Ala Val Tyr Gln Leu Thr Arg Met Cys Thr Ile Arg Met
                405                 410                 415

AGT TTT GTG AAG GGC TGG GGA GCA GAA TAT CGG AGG CAG ACA GTA ACA    1355
Ser Phe Val Lys Gly Trp Gly Ala Glu Tyr Arg Arg Gln Thr Val Thr
                    420                 425                 430

AGT ACT CCT TGC TGG ATT GAA CTT CAT CTG AAT GGC CCT CTG CAG TGG    1403
Ser Thr Pro Cys Trp Ile Glu Leu His Leu Asn Gly Pro Leu Gln Trp
                435                 440                 445

CTG GAC AAA GTA TTA ACT CAG ATG GGA TCC CCT TCA GTG CGA TGC TCA    1451
Leu Asp Lys Val Leu Thr Gln Met Gly Ser Pro Ser Val Arg Cys Ser
        450                 455                 460

AGC ATG TCG TAAACCCATC AAAGACTCGC TGTAACAGCT CCTCCGTCGT AGTATTCAT  1509
Ser Met Ser
465

GTATGATCCC GTGGACTGTT TGCTATCCAA AAATTCCAGA GCAAAACAG CACTTGAGGT   1569

CTCATCAGTT AAAGCACCTT GTGGAATCTG TTTCCTATAT TTGAATATTA GATGGGAAAA  1629

TTAGTGTCTA                                                         1639

(2) INFORMATION FOR SEQ ID NO:2:

(i) SEQUENCE CHARACTERISTICS:
        (A) LENGTH: 467 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

Met Ser Ser Ile Leu Pro Phe Thr Pro Pro Val Val Lys Arg Leu Leu
1               5                   10                  15

Gly Trp Lys Lys Ser Ala Gly Gly Ser Gly Ala Gly Gly Gly Gly Glu
            20                  25                  30

Gln Asn Gly Gln Glu Glu Lys Trp Cys Gln Lys Ala Val Lys Ser Leu
        35                  40                  45

Val Lys Lys Leu Lys Lys Thr Gly Arg Leu Asp Glu Leu Glu Lys Ala
    50                  55                  60

Ile Thr Thr Gln Asn Cys Asn Thr Lys Cys Val Thr Ile Pro Ser Thr
65                  70                  75                  80
```

```
Cys Ser Glu Ile Trp Gly Leu Ser Thr Ala Asn Thr Val Asp Gln Trp
                85                  90                  95

Asp Thr Thr Gly Leu Tyr Ser Phe Ser Glu Gln Thr Arg Ser Leu Asp
            100                 105                 110

Gly Arg Leu Gln Val Ser His Arg Lys Gly Leu Pro His Val Ile Tyr
        115                 120                 125

Cys Arg Leu Trp Arg Trp Pro Asp Leu His Ser His His Glu Leu Lys
    130                 135                 140

Ala Ile Glu Asn Cys Glu Tyr Ala Phe Asn Leu Lys Lys Asp Glu Val
145                 150                 155                 160

Cys Val Asn Pro Tyr His Tyr Gln Arg Val Glu Thr Pro Val Leu Pro
                165                 170                 175

Pro Val Leu Val Pro Arg His Thr Glu Ile Leu Thr Glu Leu Pro Pro
            180                 185                 190

Leu Asp Asp Tyr Thr His Ser Ile Pro Glu Asn Thr Asn Phe Pro Ala
        195                 200                 205

Gly Ile Glu Pro Gln Ser Asn Tyr Ile Pro Glu Thr Pro Pro Pro Gly
    210                 215                 220

Tyr Ile Ser Glu Asp Gly Glu Thr Ser Asp Gln Gln Leu Asn Gln Ser
225                 230                 235                 240

Met Asp Thr Gly Ser Pro Ala Glu Leu Ser Pro Thr Thr Leu Ser Pro
                245                 250                 255

Val Asn His Ser Leu Asp Leu Gln Pro Val Thr Tyr Ser Glu Pro Ala
            260                 265                 270

Phe Trp Cys Ser Ile Ala Tyr Tyr Glu Leu Asn Gln Arg Val Gly Glu
        275                 280                 285

Thr Phe His Ala Ser Gln Pro Ser Leu Thr Val Asp Gly Phe Thr Asp
    290                 295                 300

Pro Ser Asn Ser Glu Arg Phe Cys Leu Gly Leu Leu Ser Asn Val Asn
305                 310                 315                 320

Arg Asn Ala Thr Val Glu Met Thr Arg Arg His Ile Gly Arg Gly Val
                325                 330                 335

Arg Leu Tyr Tyr Ile Gly Gly Glu Val Phe Ala Glu Cys Leu Ser Asp
            340                 345                 350

Ser Ala Ile Phe Val Gln Ser Pro Asn Cys Asn Gln Arg Tyr Gly Trp
        355                 360                 365

His Pro Ala Thr Val Cys Lys Ile Pro Pro Gly Cys Asn Leu Lys Ile
    370                 375                 380

Phe Asn Asn Gln Glu Phe Ala Ala Leu Leu Ala Gln Ser Val Asn Gln
385                 390                 395                 400

Gly Phe Glu Ala Val Tyr Gln Leu Thr Arg Met Cys Thr Ile Arg Met
                405                 410                 415

Ser Phe Val Lys Gly Trp Gly Ala Glu Tyr Arg Arg Gln Thr Val Thr
            420                 425                 430

Ser Thr Pro Cys Trp Ile Glu Leu His Leu Asn Gly Pro Leu Gln Trp
        435                 440                 445

Leu Asp Lys Val Leu Thr Gln Met Gly Ser Pro Ser Val Arg Cys Ser
    450                 455                 460

Ser Met Ser
465
```

(2) INFORMATION FOR SEQ ID NO:3:

(i) SEQUENCE CHARACTERISTICS:

```
            (A) LENGTH: 4 amino acids
            (B) TYPE: amino acid
            (C) STRANDEDNESS: single
            (D) TOPOLOGY: linear (ii) MOLECULE TYPE: PEPTIDE (xi) SEQUENCE DESCRIPTION: SEQ ID NO:3:

Ser Ser Met Ser
1

(2) INFORMATION FOR SEQ ID NO:4:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: PEPTIDE (xi) SEQUENCE DESCRIPTION: SEQ ID NO:4:

Thr Gln Met Gly Ser Pro Ser Val Arg Cys Ser Ser Met Ser
1               5                   10

(2) INFORMATION FOR SEQ ID NO:5:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE:PEPTIDE (ix) FEATURE:
            (A) NAME/KEY: Other
            (B) LOCATION: 3
            (D) OTHER INFORMATION: Xaa = Met or Val (xi) SEQUENCE DESCRIPTION: SEQ ID NO:5:

Ser Ser Xaa Ser
1

(2) INFORMATION FOR SEQ ID NO:6:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE:PEPTIDE (xi) SEQUENCE DESCRIPTION: SEQ ID NO:6:

Lys Lys Lys Ser Ser Met Ser
1               5

(2) INFORMATION FOR SEQ ID NO:7:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: PEPTIDE (xi) SEQUENCE DESCRIPTION: SEQ ID NO:7:

Lys Lys Lys Thr Gln Met Gly Ser Pro Ser Val Arg Cys Ser Ser Met
```

```
              1               5              10              15
Ser
```

(2) INFORMATION FOR SEQ ID NO:8:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE:PEPTIDE (xi) SEQUENCE DESCRIPTION: SEQ ID NO:8:

```
Ser Ser Val Ser
1
```

(2) INFORMATION FOR SEQ ID NO:9:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: PEPTIDE (xi) SEQUENCE DESCRIPTION: SEQ ID NO:9:

```
Lys Lys Lys Ser Ser Val Ser
1               5
```

(2) INFORMATION FOR SEQ ID NO:10:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: PEPTIDE (xi) SEQUENCE DESCRIPTION: SEQ ID NO:10:

```
Thr Gln Met Gly Ser Pro His Asn Pro Ile Ser Ser Val Ser
1               5                  10
```

(2) INFORMATION FOR SEQ ID NO:11:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:11:

```
Thr Gln Met Gly Ser Pro Ser Ile Arg Cys Ser Ser Val Ser
1               5                  10
```

(2) INFORMATION FOR SEQ ID NO:12:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: PEPTIDE (xi) SEQUENCE DESCRIPTION: SEQ ID NO:12:

```
Thr Gln Met Gly Ser Pro Leu Asn Pro Ile Ser Ser Val Ser
 1               5                  10
```

(2) INFORMATION FOR SEQ ID NO:13:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: PEPTIDE (xi) SEQUENCE DESCRIPTION: SEQ ID NO:13:

```
Thr Gln Met Gly Ser Pro His Asn Pro Ile Ser Ser Val Ser
 1               5                  10
```

(2) INFORMATION FOR SEQ ID NO:14:

(i) SEQUENCE CHARACTERISTICS:
        (A) LENGTH: 1710 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 107...1507
        (D) OTHER INFORMATION:

(xi) SEQUENCE DESCRIPTION: SEQ ID NO:14:

```
CCGCGGCGGC GGAGAAGCAG CTCGCCAGCC AGCAGCCCGC CAGCCGCCGG GAGGTTCGAT        60

ACAAGAGGCT GTTTTCCTAG CGTGGCTTGC TGCCTTTGGT AAGAAC ATG TCG TCC          115
                                                Met Ser Ser
                                                 1

ATC TTG CCA TTC ACG CCG CCA GTT GTG AAG AGA CTG CTG GGA TGG AAG         163
Ile Leu Pro Phe Thr Pro Pro Val Val Lys Arg Leu Leu Gly Trp Lys
     5                  10                  15

AAG TCA GCT GGT GGG TCT GGA GGA GCA GGC GGA GGA GAG CAG AAT GGG         211
Lys Ser Ala Gly Gly Ser Gly Gly Ala Gly Gly Gly Glu Gln Asn Gly
 20                  25                  30                  35

CAG GAA GAA AAG TGG TGT GAG AAA GCA GTG AAA AGT CTG GTG AAG AAG         259
Gln Glu Glu Lys Trp Cys Glu Lys Ala Val Lys Ser Leu Val Lys Lys
             40                  45                  50

CTA AAG AAA ACA GGA CGA TTA GAT GAG CTT GAG AAA GCC ATC ACC ACT         307
Leu Lys Lys Thr Gly Arg Leu Asp Glu Leu Glu Lys Ala Ile Thr Thr
         55                  60                  65

CAA AAC TGT AAT ACT AAA TGT GTT ACC ATA CCA AGC ACT TGC TCT GAA         355
Gln Asn Cys Asn Thr Lys Cys Val Thr Ile Pro Ser Thr Cys Ser Glu
     70                  75                  80

ATT TGG GGA CTG AGT ACA CCA AAT ACG ATA GAT CAG TGG GAT ACA ACA         403
Ile Trp Gly Leu Ser Thr Pro Asn Thr Ile Asp Gln Trp Asp Thr Thr
 85                  90                  95

GGC CTT TAC AGC TTC TCT GAA CAA ACC AGG TCT CTT GAT GGT CGT CTC         451
Gly Leu Tyr Ser Phe Ser Glu Gln Thr Arg Ser Leu Asp Gly Arg Leu
100                 105                 110                 115
```

-continued

```
CAG GTA TCC CAT CGA AAA GGA TTG CCA CAT GTT ATA TAT TGC CGA TTA          499
Gln Val Ser His Arg Lys Gly Leu Pro His Val Ile Tyr Cys Arg Leu
            120                 125                 130

TGG CGC TGG CCT GAT CTT CAC AGT CAT CAT GAA CTC AAG GCA ATT GAA          547
Trp Arg Trp Pro Asp Leu His Ser His His Glu Leu Lys Ala Ile Glu
            135                 140                 145

AAC TGC GAA TAT GCT TTT AAT CTT AAA AAG GAT GAA GTA TGT GTA AAC          595
Asn Cys Glu Tyr Ala Phe Asn Leu Lys Lys Asp Glu Val Cys Val Asn
            150                 155                 160

CCT TAC CAC TAT CAG AGA GTT GAG ACA CCA GTT TTG CCT CCA GTA TTA          643
Pro Tyr His Tyr Gln Arg Val Glu Thr Pro Val Leu Pro Pro Val Leu
            165                 170                 175

GTG CCC CGA CAC ACC GAG ATC CTA ACA GAA CTT CCG CCT CTG GAT GAC          691
Val Pro Arg His Thr Glu Ile Leu Thr Glu Leu Pro Pro Leu Asp Asp
180                 185                 190                 195

TAT ACT CAC TCC ATT CCA GAA AAC ACT AAC TTC CCA GCA GGA ATT GAG          739
Tyr Thr His Ser Ile Pro Glu Asn Thr Asn Phe Pro Ala Gly Ile Glu
            200                 205                 210

CCA CAG AGT AAT TAT ATT CCA GAA ACG CCA CCT CCT GGA TAT ATC AGT          787
Pro Gln Ser Asn Tyr Ile Pro Glu Thr Pro Pro Pro Gly Tyr Ile Ser
            215                 220                 225

GAA GAT GGA GAA ACA AGT GAC CAA CAG TTG AAT CAA AGT ATG GAC ACA          835
Glu Asp Gly Glu Thr Ser Asp Gln Gln Leu Asn Gln Ser Met Asp Thr
            230                 235                 240

GGC TCT CCA GCA GAA CTA TCT CCT ACT ACT CTT TCC CCT GTT AAT CAT          883
Gly Ser Pro Ala Glu Leu Ser Pro Thr Thr Leu Ser Pro Val Asn His
245                 250                 255

AGC TTG GAT TTA CAG CCA GTT ACT TAC TCA GAA CCT GCA TTT TGG TGT          931
Ser Leu Asp Leu Gln Pro Val Thr Tyr Ser Glu Pro Ala Phe Trp Cys
260                 265                 270                 275

TCA ATA GCA TAT TAT GAA TTA AAT CAG AGG GTT GGA GAA ACC TTC CAT          979
Ser Ile Ala Tyr Tyr Glu Leu Asn Gln Arg Val Gly Glu Thr Phe His
            280                 285                 290

GCA TCA CAG CCC TCA CTC ACT GTA GAT GGC TTT ACA GAC CCA TCA AAT         1027
Ala Ser Gln Pro Ser Leu Thr Val Asp Gly Phe Thr Asp Pro Ser Asn
            295                 300                 305

TCA GAG AGG TTC TGC TTA GGT TTA CTC TCC AAT GTT AAC CGA AAT GCC         1075
Ser Glu Arg Phe Cys Leu Gly Leu Leu Ser Asn Val Asn Arg Asn Ala
            310                 315                 320

ACG GTA GAA ATG ACA AGA AGG CAT ATA GGA AGA GGA GTG CGC TTA TAC         1123
Thr Val Glu Met Thr Arg Arg His Ile Gly Arg Gly Val Arg Leu Tyr
            325                 330                 335

TAC ATA GGT GGG GAA GTT TTT GCT GAG TGC CTA AGT GAT AGT GCA ATC         1171
Tyr Ile Gly Gly Glu Val Phe Ala Glu Cys Leu Ser Asp Ser Ala Ile
340                 345                 350                 355

TTT GTG CAG AGC CCC AAT TGT AAT CAG AGA TAT GGC TGG CAC CCT GCA         1219
Phe Val Gln Ser Pro Asn Cys Asn Gln Arg Tyr Gly Trp His Pro Ala
            360                 365                 370
```

```
ACA GTG TGT AAA ATT CCA CCA GGC TGT AAT CTG AAG ATC TTC AAC AAC        1267
Thr Val Cys Lys Ile Pro Pro Gly Cys Asn Leu Lys Ile Phe Asn Asn
            375                 380                 385

CAG GAA TTT GCT GCT CTT CTG GCT CAG TCT GTT AAT CAG GGT TTT GAA        1315
Gln Glu Phe Ala Ala Leu Leu Ala Gln Ser Val Asn Gln Gly Phe Glu
            390                 395                 400

GCC GTC TAT CAG CTA ACT AGA ATG TGC ACC ATA AGA ATG AGT TTT GTG        1363
Ala Val Tyr Gln Leu Thr Arg Met Cys Thr Ile Arg Met Ser Phe Val
            405                 410                 415

AAA GGG TGG GGA GCA GAA TAC CGA AGG CAG ACG GTA ACA AGT ACT CCT        1411
Lys Gly Trp Gly Ala Glu Tyr Arg Arg Gln Thr Val Thr Ser Thr Pro
420                 425                 430                 435

TGC TGG ATT GAA CTT CAT CTG AAT GGA CCT CTA CAG TGG TTG GAC AAA        1459
Cys Trp Ile Glu Leu His Leu Asn Gly Pro Leu Gln Trp Leu Asp Lys
                    440                 445                 450

GTA TTA ACT CAG ATG GGA TCC CCT TCA GTG CGT TGC TCA AGC ATG TCA T      1508
Val Leu Thr Gln Met Gly Ser Pro Ser Val Arg Cys Ser Ser Met Ser
            455                 460                 465

AAAGCTTCAC CAATCAAGTC CCATGAAAAG ACTTAATGTA ACAACTCTTC TGTCATAGCA      1568

TTGTGTGTGG TCCCTATGGA CTGTTTACTA TCCAAAAGTT CAAGAGAGAA AACAGCACTT      1628

GAGGTCTCAT CAATTAAAGC ACCTTGTGGA ATCTGTTTCC TATATTTGAA TATTAGATGG      1688

GAAAATTAGT GTCATAAAGA TC                                              1710

(2) INFORMATION FOR SEQ ID NO:15:

(i) SEQUENCE CHARACTERISTICS:
        (A) LENGTH: 467 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO:15:

Met Ser Ser Ile Leu Pro Phe Thr Pro Pro Val Val Lys Arg Leu Leu
1               5                   10                  15

Gly Trp Lys Lys Ser Ala Gly Gly Ser Gly Ala Gly Gly Gly Gly Glu
            20                  25                  30

Gln Asn Gly Gln Glu Glu Lys Trp Cys Glu Lys Ala Val Lys Ser Leu
        35                  40                  45

Val Lys Lys Leu Lys Lys Thr Gly Arg Leu Asp Glu Leu Glu Lys Ala
50                  55                  60

Ile Thr Thr Gln Asn Cys Asn Thr Lys Cys Val Thr Ile Pro Ser Thr
65                  70                  75                  80

Cys Ser Glu Ile Trp Gly Leu Ser Thr Pro Asn Thr Ile Asp Gln Trp
                85                  90                  95

Asp Thr Thr Gly Leu Tyr Ser Phe Ser Glu Gln Thr Arg Ser Leu Asp
            100                 105                 110

Gly Arg Leu Gln Val Ser His Arg Lys Gly Leu Pro His Val Ile Tyr
        115                 120                 125
```

```
Cys Arg Leu Trp Arg Trp Pro Asp Leu His Ser His His Glu Leu Lys
    130                 135                 140

Ala Ile Glu Asn Cys Glu Tyr Ala Phe Asn Leu Lys Lys Asp Glu Val
145                 150                 155                 160

Cys Val Asn Pro Tyr His Tyr Gln Arg Val Glu Thr Pro Val Leu Pro
                165                 170                 175

Pro Val Leu Val Pro Arg His Thr Glu Ile Leu Thr Glu Leu Pro Pro
                180                 185                 190

Leu Asp Asp Tyr Thr His Ser Ile Pro Glu Asn Thr Asn Phe Pro Ala
                195                 200                 205

Gly Ile Glu Pro Gln Ser Asn Tyr Ile Pro Glu Thr Pro Pro Pro Gly
            210                 215                 220

Tyr Ile Ser Glu Asp Gly Glu Thr Ser Asp Gln Gln Leu Asn Gln Ser
225                 230                 235                 240

Met Asp Thr Gly Ser Pro Ala Glu Leu Ser Pro Thr Thr Leu Ser Pro
                245                 250                 255

Val Asn His Ser Leu Asp Leu Gln Pro Val Thr Tyr Ser Glu Pro Ala
                260                 265                 270

Phe Trp Cys Ser Ile Ala Tyr Tyr Glu Leu Asn Gln Arg Val Gly Glu
            275                 280                 285

Thr Phe His Ala Ser Gln Pro Ser Leu Thr Val Asp Gly Phe Thr Asp
    290                 295                 300

Pro Ser Asn Ser Gly Arg Phe Cys Leu Gly Leu Leu Ser Asn Val Asn
305                 310                 315                 320

Arg Asn Ala Thr Val Glu Met Thr Arg Arg His Ile Gly Arg Gly Val
                325                 330                 335

Arg Leu Tyr Tyr Ile Gly Gly Glu Val Phe Ala Glu Cys Leu Ser Asp
            340                 345                 350

Ser Ala Ile Phe Val Gln Ser Pro Asn Cys Asn Gln Arg Tyr Gly Trp
            355                 360                 365

His Pro Ala Thr Val Cys Lys Ile Pro Pro Gly Cys Asn Leu Lys Ile
    370                 375                 380

Phe Asn Asn Gln Glu Phe Ala Ala Leu Leu Ala Gln Ser Val Asn Gln
385                 390                 395                 400

Gly Phe Glu Ala Val Tyr Gln Leu Thr Arg Met Cys Thr Ile Arg Met
                405                 410                 415

Ser Phe Val Lys Gly Trp Gly Ala Glu Tyr Arg Arg Gln Thr Val Thr
            420                 425                 430

Ser Thr Pro Cys Trp Ile Glu Leu His Leu Asn Gly Pro Leu Gln Trp
            435                 440                 445

Leu Asp Lys Val Leu Thr Gln Met Gly Ser Pro Ser Val Arg Cys Ser
    450                 455                 460

Ser Met Ser
465
```